(12) United States Patent
Purcell

(10) Patent No.: US 10,111,831 B2
(45) Date of Patent: Oct. 30, 2018

(54) CHEWABLE VEHICLE FOR MOUTH ABSORPTION

(75) Inventor: Marc Purcell, Quebec (CA)

(73) Assignee: TECHNOLOGIES KHLOROS INC., Levis (Quebec) (CA)

( * ) Notice: Subject to any disclaimer, the term of this patent is extended or adjusted under 35 U.S.C. 154(b) by 268 days.

(21) Appl. No.: 14/001,677

(22) PCT Filed: Feb. 28, 2012

(86) PCT No.: PCT/CA2012/050117
§ 371 (c)(1),
(2), (4) Date: Aug. 27, 2013

(87) PCT Pub. No.: WO2012/116445
PCT Pub. Date: Sep. 7, 2012

(65) Prior Publication Data
US 2013/0337096 A1    Dec. 19, 2013

Related U.S. Application Data

(60) Provisional application No. 61/447,259, filed on Feb. 28, 2011, provisional application No. 61/591,572, filed on Jan. 27, 2012.

(51) Int. Cl.
| | |
|---|---|
| A61K 38/17 | (2006.01) |
| A61K 9/00 | (2006.01) |
| A61K 9/68 | (2006.01) |
| A61K 31/525 | (2006.01) |
| A61K 36/185 | (2006.01) |
| A61K 36/232 | (2006.01) |
| A61K 36/74 | (2006.01) |
| A61K 31/575 | (2006.01) |
| A61K 36/00 | (2006.01) |

(52) U.S. Cl.
CPC .......... *A61K 9/0056* (2013.01); *A61K 9/0058* (2013.01); *A61K 31/525* (2013.01); *A61K 31/575* (2013.01); *A61K 36/185* (2013.01); *A61K 36/232* (2013.01); *A61K 36/74* (2013.01); *A61K 38/17* (2013.01); *A61K 36/00* (2013.01)

(58) Field of Classification Search
None
See application file for complete search history.

(56) References Cited

U.S. PATENT DOCUMENTS

| | | |
|---|---|---|
| 4,150,161 A | 4/1979 | Rudolph et al. |
| 4,241,092 A | 12/1980 | Halik et al. |
| 4,254,149 A | 3/1981 | Rudolph et al. |
| 4,263,328 A | 4/1981 | Parada et al. |
| 4,271,206 A | 6/1981 | Fariel et al. |
| 4,287,216 A | 9/1981 | Mangano |
| 4,639,368 A | 1/1987 | Niazi et al. |
| 4,933,188 A * | 6/1990 | Cherukuri ............... A23G 4/06 426/3 |
| 6,200,604 B1 | 3/2001 | Pather et al. |
| 6,235,318 B1 | 5/2001 | Lombardy, Jr. et al. |
| 6,242,019 B1 | 6/2001 | Bell et al. |
| 6,602,518 B2 | 8/2003 | Seielstad et al. |
| 6,613,346 B2 | 9/2003 | Seielstad et al. |
| 6,953,592 B2 | 10/2005 | Darbyshire et al. |
| 7,244,454 B1 | 7/2007 | Zyck et al. |
| 7,887,832 B2 | 2/2011 | First et al. |
| 8,092,826 B2 | 1/2012 | Bell et al. |
| 8,133,475 B2 | 3/2012 | Tancredi et al. |
| 8,133,476 B2 | 3/2012 | Tancredi et al. |
| 9,241,908 B2 | 1/2016 | Khedkar et al. |
| 2001/0006699 A1 | 7/2001 | Bell et al. |
| 2002/0192329 A1* | 12/2002 | Corriveau ............ A23G 3/0012 426/5 |
| 2003/0021830 A1 | 1/2003 | Seielstad et al. |
| 2003/0026836 A1 | 2/2003 | Darbyshire et al. |
| 2003/0086960 A1 | 5/2003 | Seielstad et al. |
| 2003/0235613 A1 | 12/2003 | First et al. |
| 2004/0241209 A1 | 12/2004 | Kim |
| 2005/0089567 A1 | 4/2005 | First et al. |
| 2006/0078508 A1 | 4/2006 | Gebreselassie et al. |
| 2006/0078509 A1 | 4/2006 | Gebreselassie et al. |
| 2006/0211721 A1* | 9/2006 | Roberts ....................... 514/276 |
| 2006/0263475 A1 | 11/2006 | Jani et al. |
| 2006/0280834 A1 | 12/2006 | Jani et al. |

(Continued)

FOREIGN PATENT DOCUMENTS

| | | |
|---|---|---|
| CA | 2010712 A1 | 9/1990 |
| CA | 2293365 A1 | 2/1999 |

(Continued)

OTHER PUBLICATIONS 1999 http://www.foodproductdesign.com/articles/1999/11/making-a-better-coffee-creamer.aspx.*
International Search Report from PCT/CA2012/050117 dated May 4, 2012.
Written Opinion (First) from PCT/CA2012/050117 dated Jan. 30, 2013.
Official Action related to Chinese Patent Application No. 201280010696.5, dated Nov. 24, 2014.
Third Party Submission from corresponding Japanese Patent Application No. 2013-555714, dated Jan. 18, 2016. (English Translation).
English language Abstract for European Application No. 1082106; published Mar. 14, 2001.

(Continued)

*Primary Examiner* — Terry A McKelvey
*Assistant Examiner* — Catheryne Chen
(74) *Attorney, Agent, or Firm* — Millen, White, Zelano & Branigan, PC

(57) ABSTRACT

The present document describes a buccal delivery dosage form for administration of an active ingredient, including pharmaceutically, pharmacologically, or biologically active ingredients, in the mouth of a subject. The buccal delivery dosage form by-passes the gastrointestinal tract metabolism. The buccal delivery dosage form may comprise chemical permeation enhancers, excipients, texture modulators, and active ingredients.

14 Claims, 6 Drawing Sheets

(56) References Cited

U.S. PATENT DOCUMENTS

| | | |
|---|---|---|
| 2006/0286201 A1 | 12/2006 | Jani et al. |
| 2007/0237729 A1 | 10/2007 | Tancredi et al. |
| 2007/0237804 A1 | 10/2007 | Tancredi et al. |
| 2007/0237805 A1 | 10/2007 | Tancredi et al. |
| 2007/0237855 A1 | 10/2007 | Tancredi et al. |
| 2007/0237856 A1 | 10/2007 | Tancredi et al. |
| 2008/0063747 A1 | 3/2008 | Boghani et al. |
| 2008/0124283 A1 | 5/2008 | Andersen |
| 2008/0160077 A1 | 7/2008 | Borowy-Borowski |
| 2008/0187621 A1 | 8/2008 | Boghani et al. |
| 2009/0142443 A1 | 6/2009 | Robinson et al. |
| 2009/0150231 A1 | 6/2009 | Jani et al. |
| 2009/0155392 A1* | 6/2009 | Nelson .................. A61K 36/77 424/725 |
| 2010/0034871 A1 | 2/2010 | Mikkelssen et al. |
| 2010/0104689 A1 | 4/2010 | Thorengaard |
| 2010/0260818 A1* | 10/2010 | Andersen et al. ............ 424/440 |
| 2010/0266666 A1 | 10/2010 | Andersen et al. |
| 2010/0297203 A1 | 11/2010 | Tancredi et al. |
| 2011/0014132 A1 | 1/2011 | Liu |
| 2011/0086085 A1 | 4/2011 | Wenzel et al. |
| 2011/0129563 A1 | 6/2011 | Ashokan et al. |
| 2011/0305738 A1 | 12/2011 | Ladizinsky |
| 2012/0039981 A1 | 2/2012 | Pedersen et al. |
| 2012/0082755 A1 | 4/2012 | Lakkis et al. |
| 2012/0141654 A1 | 6/2012 | Bell et al. |
| 2012/0183609 A1 | 7/2012 | Colombo et al. |
| 2012/0263780 A1 | 10/2012 | Wenzel et al. |
| 2012/0321751 A1 | 12/2012 | Pedersen et al. |

FOREIGN PATENT DOCUMENTS

| | | |
|---|---|---|
| CA | 2310492 A1 | 6/1999 |
| CA | 2436010 A1 | 8/2002 |
| CA | 2451842 A1 | 1/2003 |
| CA | 2712349 A1 | 12/2003 |
| CA | 2589489 A1 | 6/2006 |
| CA | 2648313 A1 | 10/2007 |
| EP | 0017691 A1 | 10/1980 |
| EP | 0017691 B1 | 10/1980 |
| EP | 1082106 B1 | 1/2007 |
| JP | 2002-540141 A | 11/2002 |
| JP | 2004-519467 A | 7/2004 |
| JP | 2004519467 A | 7/2004 |
| JP | 2008-509922 A | 4/2008 |
| JP | 200929829 A | 2/2009 |
| JP | 2009171860 A | 8/2009 |
| JP | 2009-041714 A1 | 1/2011 |
| JP | 2011511759 A | 4/2011 |
| WO | 2002062152 A1 | 8/2002 |
| WO | 2002085402 A1 | 10/2002 |
| WO | 02/098240 A1 | 12/2002 |
| WO | 2006020754 A1 | 2/2006 |
| WO | 2007147976 A1 | 12/2007 |
| WO | 2009-050738 A2 | 4/2009 |
| WO | 2009042968 A1 | 4/2009 |
| WO | 2009153419 A1 | 12/2009 |
| WO | 2010121619 A1 | 10/2010 |
| WO | 2012106582 A2 | 8/2012 |

OTHER PUBLICATIONS

English language claim translation for Japanese Application No. 2009171860; published Aug. 6, 2009, 1 page.
English language description translation for Japanese Application No. 2009171860; published Aug. 6, 2009, 9 pages.
Notification of Reasons for Refusal for corresponding Japanese Application No. 2013-555714; published Nov. 14, 2016.
Machine translation of corresponding Japanese Application No. JP2002-540141; published Nov. 26, 2002.
Machine translation of corresponding Japanese Application No. JP2004-519467; published Jul. 2, 2004.
Machine translation of corresponding Japanese Application No. 2008-509922; published Apr. 3, 2008.
Machine translation of corresponding Japanese Application No. JP 2009-041714; published Jan. 27, 2011.
Search Report from corresponding European Patent Application No. EP 12752726, dated Jun. 24, 2014.

* cited by examiner

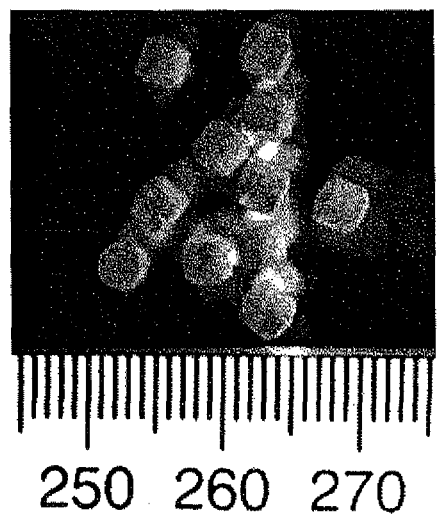
FIG. 1 Functional Khlôros Micros-spheres of 3,5 mm of diameter and 35 mg each (0,9% of Riboflavine)
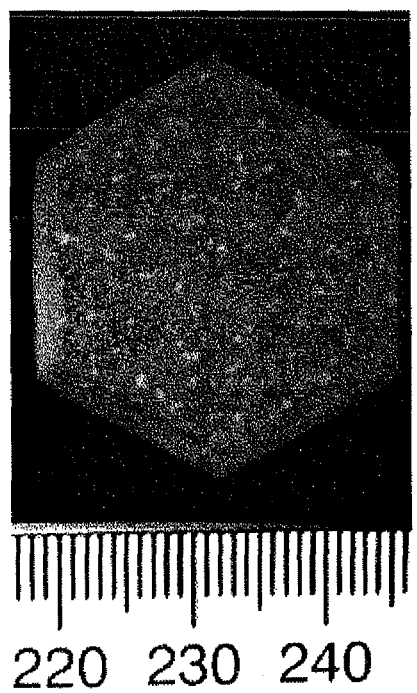
FIG. 2 Functional Khlôros Gel (made with riboflavine powder 0,9%)

CHEWABLE VEHICLE FOR MOUTH ABSORPTION

The subject matter disclosed generally relates to a chewable vehicle for absorption or uptake of active molecules in the mouth.

Digestion is the mechanical and biochemical breaking down of food and active ingredients into a smaller component that can be absorbed by the body. Bioavailability of small molecules and active ingredients is provided by their routes of absorption. Usually, the most common route to absorb food is the gastrointestinal tract (gut). The food breakdown begins with mastication followed by the transit time in the stomach. The gastric juice present in the stomach helps the degradation of food with acidity over a range of pH. In fact, the pH of an empty stomach is really acid (pH of about 1 to about 2) with an empty stomach and the transit time is in the vicinity of 30 minutes, whereas the pH is about 4 after a meal, with a transit time of 120 minutes. Following stomach transit, smaller components are headed to the gut. However, in the case of active ingredients that must be headed to the gut without degradation, a protection against stomach acidity is needed. Coatings such as enteric coatings have been used to solve this problem.

Conventionally, the oral route cannot be used for the delivery of macromolecular drugs such as proteins and peptides owing to limited transport across the epithelial membrane. This challenge can potentially be overcome through the use of chemical permeation enhancers, which affect transcellular and/or paracellular transport routes.

Dohan and Vervelle (FR 2932385; WO2009153419) describe a composition comprising original natural extracts (from vegetable or animal origin) for oral or skin application for humans or animals, characterised in that said natural extracts are microencapsulated using a spherulite technique, and in that the application is done via a gel, toothpaste, stick or mouthwash on the oral tissues (particularly on gums, cheek mucosa, and back of the tongue), or via a gel, a cream or a stick on external tissues (skin, mucosa).

Nelson and Allred (US20090155392) describe methods and systems for the sublingual and buccal administration of herbal supplements, and more particularly, to the sublingual and buccal administration of Guaraná, which allows for considerably reducing the therapeutic dose, with the additional advantage of increasing the quickness of the beneficial effects.

Borowy-Borowski (US20080160077) describes a formulation methodology for bioactive lipophilic molecules, such as Coenzyme Q10 and its reduced analogs (ubiquinols). Further provided are methods of producing soft gel capsules of this formulation.

Bell et al. (CA2293365) describes improved confectionery compositions which have a substantial reduction in the unpleasant organoleptic sensations associated with the release of functional ingredients from the confection in the oral cavity.

It would be highly desirable to be provided with a novel oral delivery vehicle for administration of active molecules to a subject which by-pass the gastro-intestinal tract.

It is an object of the present disclosure to provide a novel oral delivery for administration of active molecules to a subject which by-passes the gastro-intestinal tract.

According to an embodiment there is provided a chewable buccal delivery dosage form for oral mucosal absorption of an active ingredient in the mouth of a subject wherein said buccal delivery dosage form comprises:

at least one pH modulator to regulate the oral pH during mastication or to maximize enzymatic degradation of the dosage form in the mouth wherein the at least one pH modulator is entrapped-$CO_2$; and at least one active ingredient that is a pharmaceutically or biologically active substance.

According to an embodiment, there is provided a buccal delivery dosage form for oral mucosal absorption of an active ingredient in the mouth of a subject wherein said buccal delivery dosage form comprises:

a) at least one chemical permeation enhancer to maximize uptake of active ingredient from mouth tissues;

b) at least one excipient for suspending the active ingredient;

c) at least one texture modulator to increase retention time of said dosage form in the mouth to maximize uptake of the active ingredient; and d) at least one pH modulator to decrease or buffer the oral pH of the dosage form during mastication to maximize enzymatic degradation of the dosage form in the mouth.

According to an embodiment, there is provided a buccal delivery dosage form for administration of an active ingredient in the mouth of a subject with a by-pass of gastrointestinal tract metabolism; which may comprise at least one of the following ingredients:

a) a chemical permeation enhancer to maximize uptake of active ingredient from mouth tissues;

b) an excipient comprising a pharmaceutically inert substance for suspending the active ingredient;

c) a texture modulator to increase retention time of said dosage form in the mouth to maximize uptake of the active ingredient.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which:

FIG. 1: Functional Khlôros Micros-spheres according to the present invention of 3.5 mm in diameter and 35 mg each (0.9% of Riboflavine)

FIG. 2: Functional Khlôros Gel according to the present invention made with riboflavine powder 0.9%.

It will be noted that throughout the appended drawings, like features are identified by like reference numerals.

Figure 3:
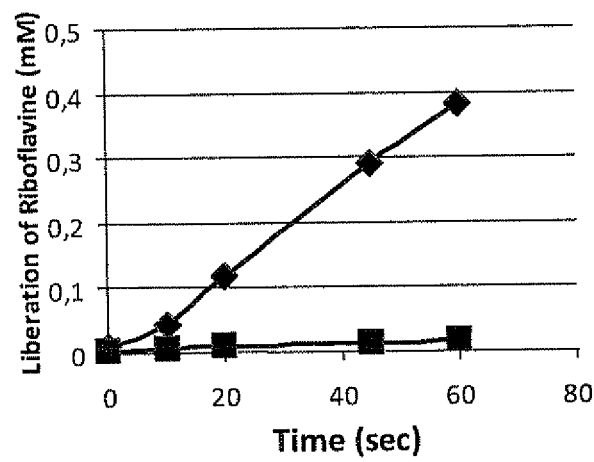
FIG. 3: Liberation of Riboflavin (0.9%) as a function of time. Passive liberation (square) and active liberation (mastication) (lozenge).

In embodiments there is disclosed a novel way to promote the absorption of active ingredients using three routes comprised in the mouth: buccal, sublingual, and local routes, which are all active during a mastication process. One faces a challenge in the case of active ingredient that have to be delivered for systemic absorption without degradation or with a controlled dispersion. The drug transport mechanism through the buccal mucosa involves two principal routes: the transcellular (intracellular) and paracellular (intercellular) pathways. The transcellular route involves the crossing of the cellular membranes with a polar and a lipid domain, whereas the paracellular route essentially implicates the passive diffusion through the extracellular lipid domain. Ionic drugs usually diffuse through the intercellular space, whereas hydrophobic drugs are able to pass through the cellular membranes.

The buccal drug delivery system has been accepted as a potential non-invasive route of drug administration, with the advantages of avoiding the first-pass metabolism, sustained therapeutic action and better patient compliance. The oral cavity is an attractive site for the delivery of drugs. The oral cavity includes the floor of the sublingual mucosa (mouth), palatal mucosa, buccal mucosa (the inside of the cheeks) and the gingival mucosa (gums). There are considerable differences in permeability between different regions of the oral cavity because of the diverse structures and functions of the different oral mucosa. In general, the permeability of the oral mucosa is greatest for the sublingual and lowest for the palatal mucosa, with the buccal mucosa having intermediate permeability. The buccal and sublingual sectors are the most appropriate for drug delivery as it is possible to realize local effect (mucosal) and systemic effect (transmucosal) of drug administration. The buccal drug delivery system also provides many advantages, such as avoiding hepatic first-pass metabolism, no presystemic metabolism, ease of administration, fast onset of action of the active ingredient(s), and unlike the skin, it has a rapid cell recovery, hence it is used for local as well as for systemic effect.

According to one embodiment of the present invention, the dosage form of the present invention may comprise permeation enhancers.

Chemical Permeation Enhancers. Membrane permeability is the limiting feature for many drugs in the progress of the buccal delivery approach. The epithelium that lines the buccal mucosa is a very effective obstacle to the permeation and hence absorption of drugs. To mitigate this barrier and to facilitate the permeation through buccal mucosa, permeation enhancers are used.

According to one embodiment of the present invention, chemical permeation enhancers work through many mechanisms. They may act by changing mucus rheology, that is, by reducing the viscosity of the mucus. Mucus forms a viscoelastic layer of varying thickness that affects drug absorption. Most chemical permeation enhancers act by disturbing the intracellular lipid packing by interaction with either lipid packing or protein components, thus increasing the fluidity of the lipid bilayer membrane. Fluidization of the plasma membrane, loosening of the tight junctions between cells, and inhibition of proteases are a few of the mechanisms.

The chemical permeation enhancer may be chosen from the chelators, surfactants, fatty acids and derivatives thereof, terpenes, cyclodextrins, azone, chitosan, and lysalbinic acid.

There are various chemical permeation enhancers, such as:

Chelators: for example EDTA, EGTA, citric acid, salicylates, N-acyl derivatives of collagen, and enamines (N-amino acyl-derivatives of 3-diketones).

Surfactants: such as sodium lauryl sulfate, polyoxyethylene-9-laurylether, and polyoxyethylene-20-cetylether; and natural surfactant such as bile salts (sodium deoxycholate, sodium glycocholate, and sodium taurocholate).

Fatty acids and their derivatives: such as sodium caprylate, sodium caprate, sodium laurate, lauric acid, oleic acid, lecithin, phospholipids >60% (phosphatidylcholine, phosphatidylethanolamine, phosphatidylinositol, phosphatidic acid) monoolein and acylcarnitines, have been shown to reduce the thickness of the unstirred water layer adjacent to the mucosal membrane, and by disrupting intercellular lipid packing.

Terpenes: is a very safe and effective class of chemical permeation enhancers obtained from natural sources (example: 1-menthol).

Cyclodextrins: cyclic oligosaccharides, are also recognized as an enhancer of the buccal permeation.

Azone: acts by creating a region of fluidity in intercellular lipids, and alcohols work by reorganizing the lipid domains and by changing protein conformation.

Chitosan and its derivates have been used to enhance the permeation of medicaments by means of the buccal route and have been found to be a potential penetration enhancer for transmucosal (intestinal, nasal, buccal and vaginal) absorption of drugs.

Lysalbinic acid was found to be a new absorption enhancer for the buccal delivery of peptide drugs.

The terms "texture and temperature modulator" or "texture modulator" are intended to mean different ingredients are used to modify the melting point (MP) temperature of a mixture, including for example, without limitations Menthol crystals, Stearic acid, Candelilla wax, Carnauba wax, and other waxes, butters and oils.

The buccal delivery dosage form may further comprise a temperature modulator to modulate temperature of the dosage form to maximize enzymatic degradation in the mouth.

Texture and temperature modulators. Different ingredients are used as texture modulators to modify the melting point (MP) temperature of a mixture. Menthol crystals (MP≈42° C.), Stearic acid (MP≈65.5° C.), Candelilla wax (MP≈67° C.), Carnauba wax (MP≈83° C.), other ingredients may be used among others, such as wax, butter and oil.

The texture of food leads to a certain sequence of chewing which continually modifies the mastication process. During the mastication process, the texture of food is dependent of the chewing sequence (i.e. mechanical influence related to the food grinding), the fluctuation of pH, the presence of saliva and the appearance of salivary enzyme, which all happen in the oral cavity in a coordinated manner to help degradation. The texture of food throughout the mastication process is also governed by the hardness and the size of the product as well as its elasticity, plasticity, stickiness, and brittleness among others. Feldman and Cryer (1999) have demonstrated in human that chewable tablets of aspirin are absorbed quicker than solid tablets. Moreover, they showed that chewable tablets were more effective at decreasing serum thromboxane B2 (acting in the cascade of clot formation). Also, it has been demonstrated that chewing on a raw carrot for a longer period of time allows more β-carotene to be liberated.

In one aspect, the excipient may be a hydrocolloid.

The hydrocolloid may be selected chosen from agar, agarose, alginates, base gum, carrageenan (iota, kappa, lambda), cellulosics, chicle, chitosan, gelatin, gellan gum, guar gum, gum arabic, locust bean gum, pectin, soybean gel, starch, whey protein, xanthan gum, and derivatives thereof.

Colloids: A colloid is a substance microscopically dispersed evenly throughout another substance. A colloidal system consists of two separate phases: a dispersed phase and a continuous phase. A hydrocolloid is defined as a colloidal system, in which the colloid particles are dispersed in water. A hydrocolloid has colloid particles spread throughout the water and depending on the quantity of water available, that system can be a gel or a solid (liquid). Hydrocolloids used in food are often polysaccharides of high molecular weight, extracted for example from plants and seaweeds or produced by microbial synthesis. The raw plant materials are then further processed, e.g. by the addition of functional side-groups, by hydrolysis and/or purification to obtain a standardized product to ensure a quality standard.

There are several hydrocolloids in food product. These include, without limitation, agar, agarose, alginates, carrageenan (iota, kappa, lambda), cellulosics, chicle, chitosan, gelatin, gellan gum, guar gum, gum arabic, gum base, locust bean gum, pectin, soybean gel, starch, whey protein, xanthan gum, derivatives thereof and combinations thereof.

In one aspect, the excipient is a gum base which comprises polyols (e.g. gum base with isomalt, gum base with sorbitol).

pH modulators: Antacids increased oesophageal pH independent of gastric pH, demonstrating that chewing antacids controls oesophageal acidity more effectively than swallowing antacid tablets.

Bicarbonate is often referred to as the major buffer of saliva. Although bicarbonate in solution can act as a pH buffer, in an open system such as the mouth, bicarbonate acts mainly to neutralize acid ($H^+$):

$$HCO_3^- + H^+ \leftrightarrows H_2CO_3 \leftrightarrows CO_2 + H_2O$$

In the mouth the concentration of carbonic acid stays constant at about 1,3 mMol/L. The pH and the bicarbonate concentration do however change. Both the pH and the bicarbonate concentration are very important and central to how saliva protects teeth. Saliva is unique in that it contains a form of carbonic anhydrase called Carbonic Anhydrase VI which is secreted by serous acinar cells of the parotid and submandibular glands. No other secreted fluid contains such an enzyme. Carbonic anhydrase drives the reaction converting carbonic acid to carbon dioxide and water (see above) which effectively collects available protons. Recent work has shown that this carbonic anhydrase forms part of the tooth pellicle where it is available to convert any protons produced by overlying dental plaque to carbon dioxide and water so long as bicarbonate is available.

The concentration of bicarbonate ($NaHCO_3$ and bicarbonate ion $HCO_3^-$) in saliva is linked to the flow rate. As the rate of saliva production increases, more bicarbonate ion is produced as a by-product of cell metabolism. Stimulated saliva contains more bicarbonate than resting saliva. This is convenient since during eating when saliva flow is increased, plaque acid is produced in higher quantities. This ensures that there is enough bicarbonate present to capture surplus protons. The dissociation of carbonic acid into bicarbonate and a proton is an important reaction (The pK of this reaction is 6.1; $pH = pK + \log [HCO_3^-]/[H_2CO_3]$).

As mentioned above, the carbonic acid concentration of saliva is constant at about 1.3 mMol/L but the bicarbonate concentration varies with the flow rate (during mastication). This is possible because of bicarbonate pumps situated in the secretory units of salivary glands. For example, 3 values of bicarbonate concentration were considered in relation with flow rate:

| Low saliva flow | → 2 mMol/L | pH = 6.29 |
| Intermediate saliva flow | → 30 mMol/L | pH = 7.46 |
| High saliva flow | → 60 mMol/L | pH = 7.76 |

During mastication, the addition of $CO_2$ (e.g. to create an effervescence sensation in the mouth) helps to regulate the optimum pH in the mouth. Adding $CO_2$ also promotes the absorption of molecules though the oral cavity. Adding $CO_2$ in the chewable vehicle is also a great indicator of the liberation of active ingredient. Effervescence may also be obtained by the use of an acid, for example citric acid, and a carbonate. According to one embodiment of the present invention, an entrapped-$CO_2$ is used. As used herein "entrapped-$CO_2$" refers to $CO_2$ that is entrapped in a suitable agent. For example, the $CO_2$ can be entrapped in suitable food product such as sugars, salts used in food products or other suitable agents. According to one embodiment of the present invention, the entrapped-$CO_2$ may be used alone. According to another embodiment of the present invention, the entrapped-$CO_2$ may be used in combination with an acid and a carbonate. In one aspect, the entrapped-$CO_2$ is $CO_2$ entrapped in sugar ($CO_2$-sugar). According to one embodiment of the present invention, the $CO_2$-sugar may be used alone. According to another embodiment of the present invention, the $CO_2$-sugar may be used in combination with an acid and a carbonate. The acid and the carbonate may be also used alone. Preferably, the $CO_2$-sugar is used, alone or in combination with an acid and carbonate. Most preferably, the $CO_2$-sugar is used alone. $CO_2$-sugar is preferably used to obtain the pH regulating effect described above.

According to one embodiment of the present invention, the $CO_2$-sugar, also known as popping sugar, comes in the shape of small bits of melted sugars (such as sucrose, lactose and glucose syrup) within which carbon dioxide has been introduced. According to the present invention, it is made by mixing ingredients including sugars, including for example without limitations lactose (milk sugar), corn syrup, glucose syrup, etc, or combinations thereof, and heating until they melt into dust, then exposing the mixture to pressurized carbon dioxide gas (about 600 pounds per square inch; or approx. 41.37 Bar) and allowing the sugar/gas mixture to cool, thereby entrapping $CO_2$ gas therein. The process causes tiny high pressure bubbles to be trapped inside the sugar. According to one embodiment of the present invention, the $CO_2$-sugar is prepared without any additional ingredient. According to another embodiment of the present invention, the $CO_2$-sugar may also be prepared from a sugar composition to which one or more ingredients have been added. According to one embodiment, the ingredient may be one or more of the active ingredients according to the present invention.

In one aspect, the pH modulator can be used to keep the pH in the mouth of the subject at the desired pH for release of the active from the dosage form and for oral mucosal absorption. As shown in examples XV and XIV, using different concentrations and granulometry of Sugar-$CO_2$ the inventor has found that under certain conditions the pH variations follows a logarithmic curve. Interestingly, one can extrapolate that entrapped-$CO_2$ can allow for a delivery of active in a subject that can be adapted based on the mastication pattern of the subject.

The mastication activity stimulates the production of saliva including the liberation of enzyme activities and favors the breaking down of the granules and the liberation of an active ingredient(s) extract in the mouth.

The fast liberation of the actives, permit their absorption by the oral cavity mucosa, through the trans- and/or paracellular routes.

The addition of $CO_2$ regulates the pH and improves the saliva constituents, such as enzymes, for a more efficient absorption and contributes to preserving or enhancing the activity of amylase, which will increase the rate of starch viscosity thinning.

The buccal delivery dosage form may further comprise a sensory indicator of active ingredient release from the dosage form. The indicator may be $CO_2$.

In one aspect, after mixing of the mixture and compression into granules, the effervescence effect is still present.

Up to 70% of the total mucin found in saliva is contributed by the minor salivary glands. At physiological pH the mucus network carries a negative charge (due to the sialic acid and sulfate residues) which may play a role in mucoadhesion. At this pH mucus can form a strongly cohesive gel structure that will bind to the epithelial cell surface as a gelatinous layer (Gandhi, R. E. and Robinson, J. R., Bioadhesion in drug delivery, *Ind. J. Pharm. Sci.*, 50:145-152, 1988). The salivary pH ranges from 5.5 to 7 depending on the flow rate. At high flow rates, the sodium and bicarbonate concentrations increase leading to an increase in the pH.

Without being bound to a specific theory, the present inventors believe that to maximize mucosal absorption, the formulation matrix of the present invention can change the ionicity and polarity of the cellular mucosa domains.

Figure 9:
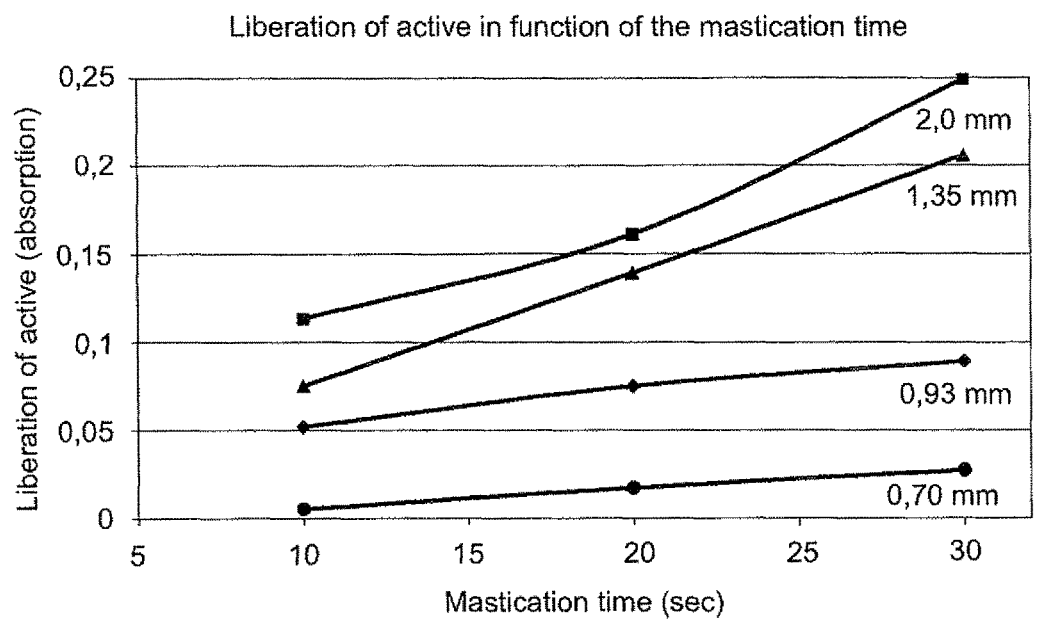
FIG. 9: Liberation of active(s) from *Hibiscus subdariffa* at 518 nm in function of the granulometry of the chew (0.7 mm; 0.93 mm; 1.35 mm; 2.0 mm).

As shown in Example XIII and on FIG. 9, the size of the particles can be used to modify the liberation of active ingredients from the dosage form. In one aspect, the biggest particle size used when preparing the dosage form of the invention is between about 0.1 mm to about 3 mm. In a further aspect, the biggest particle size used in the dosage form of the invention is preferably between about 0.5 mm to about 2 mm; more preferably between about 0.5 mm to about 2 mm and most preferably between about 0.7 mm to about 1 mm. The particle size is the size of the particles prior to compression into the desired dosage form. The particle size is measured by known methods (e.g. with sieves).

According to some embodiments, the preparation process and the selection of the ingredients of the vehicle of the present invention will allow to obtain the adequate or desired elasticity, porosity and resistance to shearing. Methods for the preparation of oral dosage forms are well known in the art. See for example Handbook of Pharmaceutical Excipients, Sixth edition 2009. Edited by R C Rowe, P J Sheskey and M E Quinn, or Remington: The Science & Practice of Pharmacy $21^{th}$ Edition, Lippincott Williams and Wilkins, Philadelphia, Pa. (2005).

In one aspect, the buccal delivery dosage form as defined herein is a buccal delivery dosage form wherein the delivery of active ingredient in the mouth of the subject is adaptable based on the mastication pattern of said subject.

According to one embodiment of the present invention, micro-tablets may contain active ingredient (up to about 80%), cellulose or other agents, such as for example, without limitations lactose monohydrate 315, or lactose monohydrate 316, or powdered manitol, $CO_2$-sugar (up to 30%), chemical permeation enhancers (lauric acid in coco oil or other chemical permeation enhancers as mentioned above, texture and temperature modulators (Candelilla wax or other, as mentioned above).

In one aspect, the dosage form of the invention have Matrix Cohesive Force (MCF) between 2 and 5. The MCF is the force of intermolecular attraction between the particles of the amalgam matrix. These forces are governed by the nature of the molecules, the compressive force, particle size and the temperature of the ingredients. The MCF is determined using an apparatus or by qualitative observation. The MCF is a factor of the texture, the cohesion and the consistency of the matrix during mastication. Typically, a high MCF is characterized by a weak cohesion between the particles and is usually indicative of a fast release. A low MCF is characterized by a strong cohesion between the particles and is usually indicative of a slower release. For a chewable dosage form, it is preferable that the matrix keeps its integrity in order to maximize the liberation and buccal mucosa absorption of the actives. In one aspect of the present invention, the MCF should be between 2 to 5 to maximize and control the liberation and buccal mucosa absorption of actives. The following table summarizes MCF and the relevant evaluation criteria.

| Matrix Cohesive Force (MCF) | Evaluation criteria |
|---|---|
| 1 | Very hard matrix - very strong cohesion particle (time stable) |
| 2 | Hard matrix - strong cohesion particle (time stable) |
| 3 | Medium to soft matrix - Strong cohesion particle (time stable) |
| 4 | Medium to soft matrix - Medium cohesion particle (time stable) |
| 5 | Medium to soft matrix - Weak cohesion particle (time stable) |
| 6 | Medium to soft matrix - Weak cohesion particle (time not-stable) |

Unless indicated otherwise weight percentages are indicated by weight of the total composition of the dosage form.

According to one embodiment, the chemical permeation enhancer and the texture modulator are mixed to prepare a modulatory mixture comprising permeation enhancers as well as texture modulators. The permeation enhancer may be employed in a ratio of about 100% to 0% texture modulator, or from about 99% permeation enhancer to about 1% texture modulator, or from about 98% permeation enhancer to about 2% texture modulator, or from about 97% permeation enhancer to about 3% texture modulator, or from about 96% permeation enhancer to about 4% texture modulator, or from about 95% permeation enhancer to about 5% texture modulator, or from about 94% permeation enhancer to about 6% texture modulator, or from about 93% permeation enhancer to about 7% texture modulator, or from about 92% permeation enhancer to about 8% texture modulator, or from about 91% permeation enhancer to about 9% texture modulator, or about 90% permeation enhancer and about 10% texture modulator. Preferably, the ratio may be about 95:5.

According to one embodiment, the buccal delivery dosage comprises from about 0.5% w/w to about 15% w/w, preferably from about 1% w/w to about 5% w/w or more preferably from about 3% w/w to about 4% w/w of the at least one chemical permeation enhancer.

According to one embodiment, the buccal delivery dosage comprises from about 20% w/w to about 90% w/w, preferably from about 50% w/w to about 85% w/w, or more preferably from about 70% w/w to about 85% w/w of the at least one excipient. In one aspect, if the excipient is a gum base with polyols, the delivery dosage will preferably comprise from about 50% w/w to about 90% w/w and more preferably from about 70% w/w to about 90% w/w. In one aspect, if the excipient is a gum base without polyols, the delivery dosage will preferably comprise from about 20% w/w to about 60% w/w.

According to one embodiment, the buccal delivery dosage comprises from about 0.1% w/w to about 6% w/w, preferably from about 0.5% w/w to about 5% w/w, more preferably from about 0.5% w/w to about 1% w/w or most preferably about 1% w/w of the at least one texture modulator.

According to one embodiment, the buccal delivery dosage form comprises from about 0.5% w/w to about 30% w/w, preferably from about 1% w/w to about 20% w/w, more preferably from about 2% w/w to about 15% w/w or most preferably about 5% w/w of the at least one pH modulator.

The buccal delivery dosage form may be chewable.

In one aspect, the active ingredient of the buccal delivery dosage as defined herein is dispersed in the mouth of the subject by mastication.

In one aspect, the active ingredient of the buccal delivery dosage as defined herein may be coated. The coating may be functional or aesthetic. In one aspect, the coating can be used to improve shelf stability (e.g. by protecting the ingredients degradation (e.g. via oxidation or light exposure). In one aspect, the coating may be a sugar coating or a film coating. In a further aspect, the coating may include an active ingredient as defined herein.

The expression "buccal delivery dosage form" is intended to mean a vehicle or carrier for administration of an active in the mouth of a subject with a by-pass of gastrointestinal tract metabolism. Such dosage forms include pill, tablet, gum, micro-tablet, micro-spheres (e.g. with diameters of about 1 µm to about 1 mm), nano-spheres (e.g. with diameters of about 100 nm, microsomes (about 1 µm to about 1 mm), gel, colloid, colloidosome, nano-capsule (e.g. with diameters of about 1 µm), pastille, paste, syrup, micronized powder, crystals, liquid, aerosol, caplet thin film or capsule.

In one aspect, the buccal delivery dosage form of the present invention substantially avoids the first-pass metabolism. Unless indicated otherwise, first-pass metabolism is defined as a pathway in which the active ingredients are modified, activated, or inactivated before they enter the systemic circulation, or are left unchanged and excreted.

The term "subject" is intended to mean any mammals, including without limitation, human, equine, bovine, caprine, feline, canine, ovine, rodents, etc.

Active Ingredients

The buccal delivery dosage form may further comprise an active ingredient. The active ingredient may be a plant extract, a natural compound or a pharmaceutical drug. It is understood that the active ingredient may have a known biological effect.

The term "active ingredient" is intended to mean any pharmaceutically, pharmacologically, or biologically active substance such as a pharmaceutical drug, or a vitamin that is biologically active. These include without limitations enzyme inhibitors (e.g. carbonic anhydrase inhibitors), ion channel blockers (e.g. calcium channel blockers), antacids, amino acid, reflux suppressant, antiflatulents, antidopaminergics, proton pump inhibitors, $H_2$-receptor antagonists, cytoprotectants, prostaglandin and prostaglandin analogues, laxatives, antispasmodics, antidiarrheals, bile acid sequestrants, opioids, beta-receptor blocker, diuretics, cardiac glycosides, antiarrhytmics, nitrate, antiangials, vasoconstrictor, vasodilators, peripheral activators, ACE inhibitors, angiotensin receptor blockers, alpha-blocker, anticoagulants, heparin, antiplatelet drugs fibrinolytics, anti-hemophilic factors, haemostatic drugs, hypolipidaemic agents, statins, hyphotics, anaesthetics, antipsychotics, antidepressants (such as tricyclic antidepressant, monoamine oxidase B inhibitors, lithium salts and selective serotonin reuptake inhibitors), antiemetics, anticonvulsants/antiepileptics, anxiolytics, barbiturates, folic acid, phenolic compounds, movement disorder drugs, fatty acids (such as oleic acid, linoleic acid, Myristoleic acid, Palmitoleic acid, Sapienic acid, α-Linolenic acid or omega-3, Arachidonic acid, Eicosapentaenoic acid, Erucic acid, Docosahexaenoic acid, Lauric acid, Myristic acid, Palmitic acid, Stearic acid, Arachidic acid, stimulants, benzodiazepine, cyclopyrrolones, dopamine agonists/antagonists, antihistamines, bromide, scopolamine, cholinergics, anticholinergics, emetics, cannabinoids, 5-HT antagonists, NSAIDs (such as COX-2 selective inhibitors), opioids, orphans drugs (such as paracetamol), muscle relaxant, neuromuscular drugs, anticholinesterases, adrenergic blockers, antibiotics, aminoglycosides, sulfa drugs, fluoroquinolones, antiviral drugs, anti-fungal, corticosteroids, mast cell inhibitors, prostaglandin agonists/inhibitors, steroids, antiseptics, anesthetics, androgens, antiandrogens, gonadotropin, human growth factor, insulin, antidiabetics, thyroid hormones, antithyroid drugs, calcitonin, diphosphonate, vasopressin analogues, quinolones, 5-alpha reductase inhibitor, selective alpha-1 blockers, sildenafils, tadalafils, fertility drugs, hormonal contraception, ormeloxifene, antifibrinolytics, follicle stimulating hormone, luteinising hormone, gamolenic acid, gonadotropin release inhibitor, progestin, oestrogen, gonadorelin, clomiphene, tamoxifen, diethyl stilbestrol, antileprotics, antituberculous drugs, antimalarials, anthelmintics, amoebicides, antivirals, antiprotozoals, vaccines, immunoglobulins, immunosuppressants, interferons, monoclonal antibodies, anti-allergics, cytotoxic drugs, therapeutic antibodies, somatostatin inhibitors, recombinant interleukins, G-CSF, erythropoietin, vitamins, pigments, antioxidant, laxative, mineral supplements (such as calcium, chromium, folate, iron, magnesium, selenium, nitrate . . . ), natural compounds, including without limitations Bilobalide, Ginkgolide, hypericine, Hyperforin, Silymarine, Silibinin, a Lignan, Diosgenine, curcumin, hydroxycitric acid, eleutherocide B, eleutherocide E, a phytosterol, a saponin, sarsapic acid, yohimbine, gingerol, phytosterols including without limitations diosgenine, brassicasterol, campaestrol, 5α-cholestane, β-sitosterone, β-sitosterol, stigmasterol, etc.

The plant extract may be chosen from Absinthe (*Artemisia absinthum*), Alfalfa (*Medicago sativa*), Aloe (Aloe barbadensis), Angelica (Angelica archangelica and sinensis), Anise (Pimpinella anisum), Arnica (Arnica montana), Ashwaganda (Withania somnifera), *Astragalus* (Astragalus membranaceus), Betony (Stachys/Betonica officinalis), Bilberry/Huckleberry (*Vaccinium* spp.), Bitter melon fruit (*Momordica charantia*), Black cohash (*Cimicifuga racemosa*), Bladderwrack (Fucus versiculosus), Blessed thistle (Cnicus benedictus), Blue cohosh (Caulophyllum thalictroides), Boneset (Eupatorium perforatum), Burdock (Arctium lappa), *Caesalpinia benthamiana*, Calendula (*Calendula officinalis*), California poppy (Eschscholzia californica), Caraway (Carum carvi), Cardamom (Elettaria cardamomum), Cascara (Rhamnus purshiana), Catnip (*Nepeta cataria*), Cayenne (Capsicum frutescens), Cedar, Western (*Thuja plicata* or occidentalis), Chamomile (Matricaria recutita), Chaparral (Larrea mexicana), Chaste tree berry (Vitex agnus castus), Chickweed (*Stellaria media*), Cinnamon (*Cinnamomum* spp.), Cleavers (Galium aparine), Coltsfoot (Tussilago farfara), Comfrey (Symphytum officinalis), Corn silk (*Zea mays*), *Corynanthe yohimbe*, Cramp bark (Viburnum opulus), Dandelion (Taraxacum officinalis), Devil's club (Oplopanax horridus), *Dioscorea villosa*, Dong quai (Angelica sinensis), *Echinacea* (*Echinacea* spp.), Elder flowers (*Sambucus* spp.), Elecampane (Inula helenium), Eyebright (Euphrasia officinalis), Fadogia agrestis, Fennel (Foeniculum vulgare), Fenugreek (Trigonella foenum-graecum), Feverfew (Tanacetum parthenium), Flax seed (*Linum usitatissimum*), *Garcinia Cambogia*, Garlic (Allium sativa), Geranium (Geranium maculatum), Ginger (Zingiber officinalis), Ginkgo (*Ginkgo biloba*), Ginseng (*Panax* spp.), Goldenrod (*Solidago* spp.), Goldenseal (Hydrastis canadensis), Gotu kola (Centella asiatica), Gravel root (Eupatorium purpureum), Hawthorne (*Crataegus* spp.), *Hibiscus subdariffa*, Hops (*Humulus lupulus*), Horehound (Marrubium vulgaris), Horsetail (Equisetum arvense), *Hippophae rhamnoides*, Hyssop (Hyssopus officinalis), Kava kava (Piper methysticum), Lady's mantle (Alchemilla vulgaris), Lemon balm (*Melissa officinalis*), *Lepidium meyenii*, Licorice (Glycyrrhiza glabra), Linden flower (*Tilia* spp.), Lobelia (Lobelia inflata), Lomatium (Lomatium dissectum), Lungwort (Sticta pulmonaria), Marshmallow (Althea officinalis), *Massularia acuminate*, Meadowsweet (Filipendula ulmaria), *Microdesmis keayana*, Milk thistle (Silybum marianum), *Morinda citrifolia*, Motherwort (Leonurus cardiaca), *Mucuna pruriens*, Mugwort (*Artemisia vulgaris*), Mullein (Verbascum thapsus), Myrrh gum (*Commiphora myrrha*), Nettle (*Urtica* spp.), Noni (*Morinda citrifolia*), Nopal (Opuntia *ficus indica*), Oat (*Avena sativa*), *Oenothera biennis*, Old man's beard, *Usnea* (*Usnea* spp.), Oregon grape root and barberry (*Mahonia* spp.), Osha (Ligusticum porteri), Parsley (Petroselinum crispum), Passionflower (Passiflora incarnata), Peppermint (*Mentha piperita*), Plantain (*Plantago* spp.), Poplar buds (*Populus* spp.), Red clover (*Trifolium pratense*), Red raspberry (Rubus idaeus), Red root (Ceanothus americanus), *Rhodiola Rosea*, Rosemary (*Rosmarinus officinalis*), Sage (*Salvia officinalis*), Saint John's wort (Hypericum perforatum), Saw palmetto (Serenoa repens), Sea-buckthorn (*Hippophae rhamnoides*), Sesame seed (*Sesamum indicum*), Siberian ginseng (Eleutherococcus senticosus), Skullcap (Scutellaria laterifolia), Slippery elm (*Ulmus* spp. (rubra, fulva)), Thyme (*Thymus vulgaris*), *Triblus terrestris*, Tumeric (*Curcuma longa*), *Thuya occidentalis*, Uva ursi (Arctostaphylos uva ursi), Valerian (Valeriana officinalis), Vervain (Verbena officinalis), White oak bark (*Quercus alba*), Wild cherry (*Prunus* spp.), Willow (*Salix* spp.), Yarrow (Achillea millefolium), Yellow dock (Rumex crispus/obtusifolius), or combinations thereof.

The active ingredient may also be specific natural compounds, including without limitations Astaxanthin, Bilobalide, Biotine, Catechine, Choline, Coenzyme $Q_{10}$, Curcumine, Lecithin, Conjugated linoleic acid, Ginkgolide, Glucosamine, Hypericine, Hyperforn, Silymarine, Silibinin, a Lignan, Diosgenine, hydroxycitric acid, eleutherocide B, Eleutherocide E, L-carnitine, Leucine, Megastigmane glycoside, Melatonine, Niacinamide, Niacine, Omega-3, Pantothenic acid, a phytosterol, Phospholipids, Pinolenic acid, Resveratrol, Riboflavine, Rosiglitazone, Serotonin, Theobromine, Theophylline, Thiamine, g-aminobutyric acid (pathway), a saponin, sarsapic acid, Vitamin $B_{12}$, Yohimbine, gingerol, or combinations thereof.

The phytosterol may be chosen from diosgenine, brassicasterol, campaestrol, 5α-cholestane, β-sitosterone, β-sitosterol, stigmasterol, or combinations thereof.

The active ingredient may be chosen from Colostrum (Shing et al, J. Appl. Physiol. 2007. Effects of bovine colostrum supplementation on immune variables in highly trained cyclists. 102, 1113-1122).

According to some embodiments of the present invention, the active ingredients are plant extracts. Preferably, the plant extracts include without limitations. Preferably, the plant extracts include without limitations Absinthe (*Artemisia absinthum*), Acai, Alfalfa (*Medicago sativa*), Aloe (Aloe barbadensis), Angelica (Angelica archangelica and sinensis), Anise (Pimpinella anisum), Arnica (Arnica montana), Ashwaganda (Withania somnifera), *Astragalus* (Astragalus membranaceus), Betony (Stachys/Betonica officinalis), Bilberry/Huckleberry (*Vaccinium* spp.), Bitter melon fruit (*Momordica charantia*), Black cohash (*Cimicifuga racemosa*), Bladderwrack (Fucus versiculosus), Blessed thistle (Cnicus benedictus), Blue cohosh (Caulophyllum thalictroides), Boneset (Eupatorium perforatum), Burdock (Arctium lappa), *Caesalpinia benthamiana*, Calendula (*Calendula officinalis*), California poppy (Eschscholzia californica), Caralluma fibriata, Caraway (Carum carvi), Cardamom (Elettaria cardamomum), Cascara (Rhamnus purshiana), Catnip (*Nepeta cataria*), Cayenne (Capsicum frutescens), Cedar, Western (*Thuja plicata* or occidentalis), Chamomile (Matricaria recutita), Chaparral (Larrea mexicana), Chaste tree berry (Vitex agnus castus), Chickweed (*Stellaria media*), Cinnamon (*Cinnamomum* spp.), Cleavers (Galium aparine), Coltsfoot (Tussilago farfara), Comfrey (Symphytum officinalis), Corn silk (*Zea mays*), *Corynanthe yohimbe*, Cramp bark (Viburnum opulus), *Curcuma*, Dandelion (Taraxacum officinalis), Devil's club (Oplopanax horridus), *Dioscorea villosa*, Dong quai (Angelica sinensis), *Echinacea* (*Echinacea* spp.), Elder flowers (*Sambucus* spp.), Elecampane (Inula helenium), Eyebright (Euphrasia officinalis), Fadogia agrestis, Fennel (Foeniculum vulgare), Fenugreek (Trigonella foenum-graecum), Feverfew (Tanacetum parthenium), Flax seed (*Linum usitatissimum*), *Garcinia Cambogia*, Garlic (Allium sativa), Geranium (Geranium maculatum), Ginger (Zingiber officinalis), Ginkgo (*Ginkgo biloba*), Ginseng (*Panax* spp.), Goldenrod (*Solidago* spp.), Goldenseal (Hydrastis canadensis), Gotu kola (Centella asiatica), Gravel root (Eupatorium purpureum), Hawthorne (*Crataegus* spp.), *Hibiscus subdariffa*, Hops (*Humulus lupulus*), Horehound (Marrubium vulgaris), Horsetail (Equisetum arvense), *Hippophae rhamnoides*, Hyssop (Hyssopus officinalis), Kava kava (Piper methysticum), Lady's mantle (Alchemilla vulgaris), Lemon balm (*Melissa officinalis*), *Lepidium meyenii*, Licorice (Glycyrrhiza glabra), Linden flower (*Tilia* spp.), Lobelia (Lobelia inflata), Lomatium (Lomatium dissectum), Lungwort (Sticta pulmonaria), Marshmallow (Althea officinalis), *Massularia acuminate*, Meadowsweet (Filipendula ulmaria), *Microdesmis keayana*, Milk thistle (Silybum marianum), *Morinda citrifolia*, Motherwort (Leonurus cardiaca), *Mucuna pruriens*, Mugwort (*Artemisia vulgaris*), Mullein (Verbascum thapsus), Myrrh gum (*Commiphora myrrha*), Nettle (*Urtica* spp.), Noni (*Morinda citrifolia*), Nopal (*Opuntia ficus indica*), Oat (*Avena sativa*), *Oenothera biennis*, Old man's beard, *Usnea* (*Usnea* spp.), Oregon grape root and barberry (*Mahonia* spp.), Osha (Ligusticum porteri), Parsley (Petroselinum crispum), Passionflower (Passiflora incarnata), Peppermint (*Mentha piperita*), Plantain (*Plantago* spp.), Poplar buds (*Populus* spp.), Red clover (*Trifolium pratense*), Red raspberry (Rubus idaeus), Red root (Ceanothus americanus), *Rhodiola Rosea*, Rosemary (*Rosmarinus officinalis*), Sage (*Salvia officinalis*), Saint John's wort (Hypericum perforatum), Saw palmetto (Serenoa repens), Sea-buckthorn (*Hippophae rhamnoides*), Sesame seed (*Sesamum indicum*), Siberian ginseng (Eleutherococcus senticosus), Skullcap (Scutellaria laterifolia), Slippery elm (*Ulmus* spp. (rubra, fulva)), Thyme (*Thymus vulgaris*), *Triblus terrestris*, Tumeric (*Curcuma longa*), *Thuya occidentalis*, Uva ursi (Arctostaphylos uva ursi), Valerian (Valeriana officinalis), Vervain (Verbena officinalis), White oak bark (*Quercus alba*), Wild cherry (*Prunus* spp.), Willow (*Salix* spp.), Yarrow (Achillea millefolium), Yellow dock (Rumex crispus/obtusifolius), Yerba mate or combinations thereof.

The active ingredient may also be specific natural compounds, including without limitations Astaxanthin, Bilobalide, Biotine, Catechine, Choline, Coenzyme $Q_{10}$, Curcumine, Lecithin, Conjugated linoleic acid, Ginkgolide, Glucosamine, Hypericine, Hyperforin, Silymarine, Silibinin, a Lignan, Diosgenine, hydroxycitric acid, eleutherocide B, Eleutherocide E, L-carnitine, Leucine, Megastigmane glycoside, Melatonine, Niacinamide, Niacine, Omega-3, Pantothenic acid, a phytosterol, Phospholipids, Pinolenic acid, Resveratrol, Riboflavine, Rosiglitazone, Serotonin, Theobromine, Theophylline, Thiamine, g-aminobutyric acid (pathway), a saponin, sarsapic acid, Vitamin $B_{12}$, Yohimbine, gingerol, or combinations thereof.

The active ingredient may be chosen from Bilobalide, Ginkgolide, hypericine, hyperforin, Silymarine, Silibinin, a Lignan, Diosgenine, hydroxycitric acid, eleutherocide B, eleutherocide E, a phytosterol, a saponin, sarsapic acid, yohimbine, gingerol, or combinations thereof.

The phytosterol may be chosen from diosgenine, brassicasterol, campaestrol, 5α-cholestane, β-sitosterone, β-sitosterol, stigmasterol, or combinations thereof.

The active ingredient may be a *Hypericum perforatum* extract.

The active ingredient may be hypericine, hyperforin, or both.

The active ingredient may be a *Hibiscus subdariffa* extract.

The active ingredient may be a hydroxycitric acid.

The active ingredient may be an *Eleutherococcus senticosus* extract.

The active ingredient may be eleutherocide B, eleutherocide E, or both.

The active ingredient may be an *Oenothera biennis* extract.

The active ingredient may be a phytosterol chosen from diosgenine, bras sicasterol, campaestrol, 5α-cholestane, β-sitosterone, β-sitosterol, stigmasterol, or combinations thereof.

The active ingredient may be a *Silybum marianum* extract.

The active ingredient may be Silymarine, Silibinin or both.

The active ingredient may be a *Zingiber officinale* extract.

The active ingredient is gingerol.

Uses and Methods

According to another embodiment of the present invention there is provided therapeutic methods as described herein comprising administering a therapeutically effective amount of a dosage form according to the present invention.

According to another embodiment of the present invention dosage form according to the present invention are useful for therapeutic uses as described herein.

The methods and uses include improving cognition, decreasing appetite, decreasing fatigue, reducing menstrual troubles, reducing hangover, reducing nausea, reducing nausea, reducing the stress, as an aphrodisiac or for pain relief.

According to another embodiment of the present invention there is provided a method of improving cognition comprising administering a therapeutically effective amount of a dosage form according to the present invention.

According to another embodiment of the present invention there is provided a method of decreasing appetite comprising administering a therapeutically effective amount of a dosage form according to the present invention.

According to another embodiment of the present invention there is provided a method of decreasing fatigue comprising administering a therapeutically effective amount of a dosage form according to the present invention.

According to another embodiment of the present invention there is provided a method of reducing menstrual troubles comprising administering a therapeutically effective amount of a dosage form according to the present invention.

According to another embodiment of the present invention there is provided a method of reducing hangover comprising administering a therapeutically effective amount of a dosage form according to the present invention.

According to another embodiment of the present invention there is provided a method of reducing nausea comprising administering a therapeutically effective amount of a dosage form according to the present invention.

According to another embodiment, of the present invention there is provided a method for reducing nausea comprising administering a therapeutically effective amount of a dosage form according to the present invention.

According to another embodiment, of the present invention there is provided a method for reducing stress comprising administering a therapeutically effective amount of a dosage form according to the present invention.

According to another embodiment, of the present invention there is provided administering a therapeutically effective amount of a dosage form according to the present invention as an aphrodisiac.

According to another embodiment, of the present invention there is provided administering a therapeutically effective amount of a dosage form according to the present invention for pain relief.

According to another embodiment of the present invention there is provided a use of a dosage form according to the present invention for improving cognition.

According to another embodiment of the present invention there is provided a use of a dosage form according to the present invention for decreasing appetite.

According to another embodiment of the present invention there is provided a use of a dosage form according to the present invention for decreasing fatigue.

According to another embodiment of the present invention there is provided a use of a dosage form according to the present invention for reducing menstrual troubles.

According to another embodiment of the present invention there is provided a use of a dosage form according to the present invention for reducing hangover.

According to another embodiment of the present invention there is provided a use of a dosage form according to the present invention for reducing nausea.

According to another embodiment of the present invention there is provided a use of a dosage form according to the present invention for the preparation of a medicament for improving cognition.

According to another embodiment of the present invention there is provided a use of a dosage form according to the present invention for the preparation of a medicament for decreasing appetite.

According to another embodiment of the present invention there is provided a use of a dosage form according to the present invention for the preparation of a medicament for decreasing fatigue.

According to another embodiment of the present invention there is provided a use of a dosage form according to the present invention for the preparation of a medicament for reducing menstrual troubles.

According to another embodiment of the present invention there is provided a use of a dosage form according to the present invention for the preparation of a medicament for reducing hangover.

According to another embodiment of the present invention there is provided a use of a dosage form according to the present invention for the preparation of a medicament for reducing nausea.

In use, the oral dosages of the present invention may be employed for various therapeutic and/or nutraceutic improvements.

For example, *Hypericum perforatum* extract, and/or hypericine, hyperforin, or both may be used for improving cognition, or decreasing the loss of cognition.

According to another embodiment, *Hibiscus subdariffa* extract and/or hydroxycitric acid may be used for decreasing appetite and weight control.

According to another embodiment, *Eleutherococcus senticosus* extract and/or eleutherocide B, eleutherocide E, melatonine and polyphenol may be used for decreasing fatigue.

According to another embodiment, the *Oenothera biennis* extract and/or phytosterol chosen from diosgenine, brassicasterol, campaestrol, 5α-cholestane, β-sitosterone, β-sitosterol, stigmasterol, or combinations thereof may be used for reducing menstrual troubles.

According to another embodiment, the *Silybum marianum* extract and/or Silymarine, Silibinin or both and also curcumin, choline, lecithin and Hovenia dulcis may be used for reducing hangover.

According to another embodiment, the *Zingiber officinale* extract and/or gingerol and also Coenzyme $Q_{10}$, may be used for reducing nausea.

According to another embodiment, the melatonine, theanine and ginger tea may be used for reducing the stress.

According to another embodiment, Yohimbine may be used as an aphrodisiac.

According to another embodiment, the glucosamine may be used for pain relief.

The present invention will be more readily understood by referring to the following examples which are given to illustrate the invention rather than to limit its scope.

EXAMPLE I

Preparation of a Functional Amalgam

Preparation of the Active Ingredient(s) Mixture

Dry powder form: plant parts (including root, bark, fruit, leaf, flower, stem, seed, rhizome, etc) are cut into small part and dried to obtain a humidity factor of less than 15%. The dry parts are grinded to obtain a fine powder.

Oil form (Oenothera biennis for example) are provided as cold-pressed extraction.

Reduction or elimination of complex sugar (cellulose, hemi-cellulose . . . ). Preparation of tinctures: A solution of about 15% to about 30% w/v of powdered dry plant parts and/or of the oil extract, in 70% ethanol is prepared and agitated for about 2 hours or more. The solution is filtered through a filter or mesh and the remaining ethanol is evaporated by heating (79° C.) or by using a desiccator. Preparation of a modulatory mixture comprising permeation enhancer and a modulator of melting point. To prepare the modulatory mixture, 95 g of coconut oil (containing 42-52% of lauric acid; melting point 25° C.) is mixed with 5 g of Candelilla wax. The 95:5 modulatory mixture is melted at 75°-80° C. and mixed until an homogenous composition is obtained. As a function of the concentration of active ingredient and other constituents of the final mixture, the ratio of the modulatory mixture may differ to obtain a melting point of 36° C., the temperature of the mouth.

Preparation of $CO_2$-Sugar $CO_2$-sugar is made by mixing ingredients including sugars, including for example without limitations lactose (milk sugar), corn syrup, glucose syrup, etc, or combinations thereof, and heating until they melt into dust, then exposing the mixture to pressurized carbon dioxide gas (about 600 pounds per square inch; or approx. 41.37 Bar) and allowing the sugar/gas mixture to cool, thereby entrapping $CO_2$ gas therein. The process causes tiny high pressure bubbles to be trapped inside the candy. According to one embodiment of the present invention, the $CO_2$-sugar is prepared without any additional ingredient. According to another embodiment of the present invention, the $CO_2$-sugar may also be prepared from a sugar composition to which one or more ingredients have been added. According to one embodiment, the ingredient may be one or more of the active ingredients according to the present invention.

Preparation of the Functional Amalgam

50% of functional ingredient, 15% of $CO_2$-sugar, 10% of modulatory mixture, 24% of cellulose and 1% of lubricant.

Preparation of Functional Micro-Spheres

Pre-mix the active ingredient with cellulose and:
a) Dissolve the modulatory mixture in pre-heated alcohol (denatured ethylic alcohol) at 55° C.;
b) Mix the active ingredient(s) with the cellulose (microcrystalline Ph 100-200) in a commercial blender;
c) In the running blender, add the mix prepared in a);
d) Let the alcohol evaporate in an oven at 40° C.;
e) Sift the mixture through a 20 mesh sieve;
f) Add the $CO_2$-sugar to the mixture;
g) Add more cellulose to obtain a good flow;
h) Add the lubricant (stearate magnesium)

Composition Percentages

Modulatory mixture: up to 10%, (100% permeation enhancer/0 texture modulator up to 90% permeation enhancer/10% texture modulator);
Cellulose: 10-40%
Active ingredient: up to 80%;
$CO_2$-sugar: up to 20%,
Lubricant: up to 2%.

Furthermore, adhesives such as povidones (e.g. Polyvinylpyrrolidone) could also be included up to 3% and help the granulation process.

To obtain a free running preparation: Grind the sugar-$CO_2$ to obtain fragment of 1 mm or less and mix to the active ingredient. Pre-heat the modulatory mixture amalgam to 50° C., let it cool down to 40° C. and mix with the previous mixture. Compressed the mixture in an multipunch tabletting machine to obtain micro-spheres of 35 mg (approximately 4-5 mm in diameter). The compression force may be adjusted according to the active ingredient liberation profile.

Preparation of Spheroids

As the starting material, the functional amalgam is used.

The powder is then extruded to form filaments of about 0.5 mm to 4 mm. The filaments are batched and dropped onto a spinning wheel where they are fractured into short lengths. The speed, batch size, process time are controlled to form spheres of specific sizes (from about 0.5 mm to about 2 mm).

EXAMPLE II

Preparation of Chewable Gel

Mix pure gelatin with water to a concentration of 14% w/v and heat the mixture up to 50° C. with continuous stifling; once the mixture is fully liquid, remove from heat and pour into mold to obtain a gel of 2-3 mm thickness. The gel is allowed to cool at room temperature for 10 minutes and plated at 4° C. for 10 minutes The functional amalgam, on a powder form, is introduced directly with the gelatin powder. The functional microspheres are introduced directly in the gel during the cool-down step.

EXAMPLE III

Chewing Gum a) Base gum (chicle or butadiene, 49-80%-styrene, 20-51%, rubber blended with or substitute for poly-isobutylene+polyvinyl acetate or isobutylene-isoprene) is heated at 120° C. (Warm both pans for approximately 10 minute).
b) Remove the warmed base gum from oven and immediately make an indentation in the gum base, add warmed wax and/or hydrogenated vegetable oil (1-5%) and/or lecithin or glycerol mono stearate (1-5%) and/or coconut oil.
c) Mix thoroughly. Stabilized the base gum with BHT or BHA (0.25-0.5%).
d) Rewarm the gum base to 120° C. for ten minutes.
e) Let cool down and add calcium carbonate or talc (5-20%) into the softened base.
f) Rewarm at 120° C. for ten minutes.
g) During the cool down step, add Khlôros amalgam or functional micro-spheres or spheroids.

EXAMPLE IV

Liberation of Active Ingredient (Riboflavin)

Material:
Khlôros functional gel (see examples I and II);
0.9% Riboflavin;
Reactional media: 10 ml of $H_2O$/gel;
Passive liberation of active ingredient (Riboflavin): no treatment on the gel;
Artificial mastication (active liberation): mimic the action of mastication →compression and soft shearing;
Detection of the liberation of riboflavin and conversion in mM by the spectroscopic evaluation at 445 nm.
Comparison of Passive and Active Liberation of Riboflavin After only 60 seconds, the liberation of riboflavin is 23 times more effective after artificial mastication compare to passive liberation (see FIG. 3).

Figure 4:
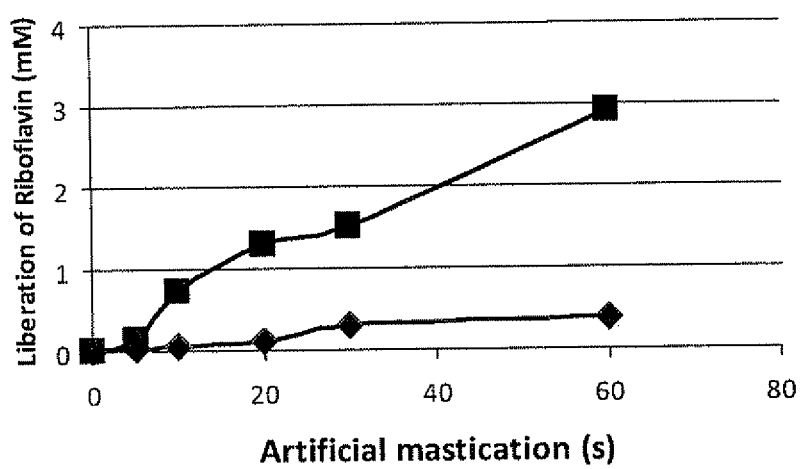
FIG. 4: Liberation of riboflavin from a gel (0.9% riboflavin) prepared with riboflavin powder (lozenge) and with Khlôros microspheres according to the present invention (square).

Liberation of riboflavin from a functional gel made with microspheres riboflavin and powder riboflavin. Both gel contain 0.9% of riboflavin. The preparation of functional gel with Khlôros microspheres instead of powder riboflavin confer a liberation of active 7.7 times more effective, after 60 seconds of artificial mastication (see FIG. 4).

EXAMPLE V

Evaluation of the Liberation of Active According to the Artificial Mastication Methods The liberation of active ingredients from a complex preparation may be increased with the proper gel. The material is a functional gel (see example II) with powder extract from Hibiscus sabdariffa flower (9%).

Artificial mastication methods. 2 methods were used to mimic mastication: 1° medium compression with soft shearing (see example III) and 2° medium compression with hard shearing (mimic the shearing by teeth).

Detection of the liberation of active ingredient from Hibiscus. The absorbance at 518 nm is measured by a spectrophotometer.

Figure 5:
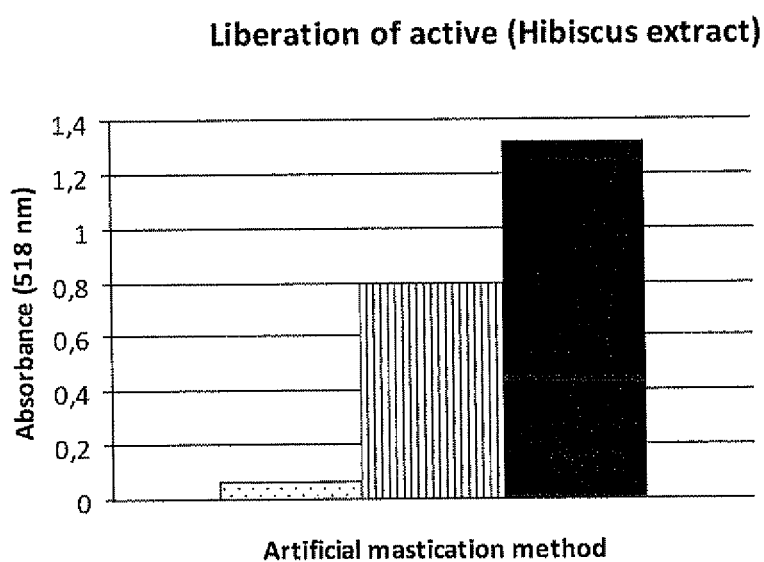
FIG. 5: Liberation of actives from functional Khlôros gel according to the present invention (9% of *Hibiscus subdariffa* granulated flower powder) as a function of artificial mastication method. The active is detected by absorbance at 518 nm. Control, no artificial mastication (dot), medium compression and soft shearing (line) and medium compression and hard shearing (black).

Using the Khlôros functional gel, compared to passive diffusion (no mastication) the liberation of actives is 12 times more efficient when using artificial mastication method 1, after 60 seconds. When using mastication method 2, the liberation of actives is 20 times more efficient compared to passive diffusion of actives (see FIG. 5).

EXAMPLE VI

Comparison of the Mouth Absorption of Active(s) with and without Mastication

Protocol
a. Weigh a fixed quantity of the Khlôros functional amalgam (with 50% of active);
b. Ask the volunteer to clean his mouth with 10 ml of $H_2O$ prior to testing;
c. Set the amalgam on the volunteer's tongue;
d. The volunteer will have to chew or let the sample on his tongue for a predetermined period of time (30 secs-60 secs-90 secs);
e. The volunteer will have to avoid swallowing the sample;
f. Collect saliva of the volunteer including the sample in a beaker;

g. Ask the volunteer to rinse his mouth with 10 ml of $H_2O$ (2×);
h. Add $H_2O$ to reach 30 ml and shake thoroughly.

Figure 6:
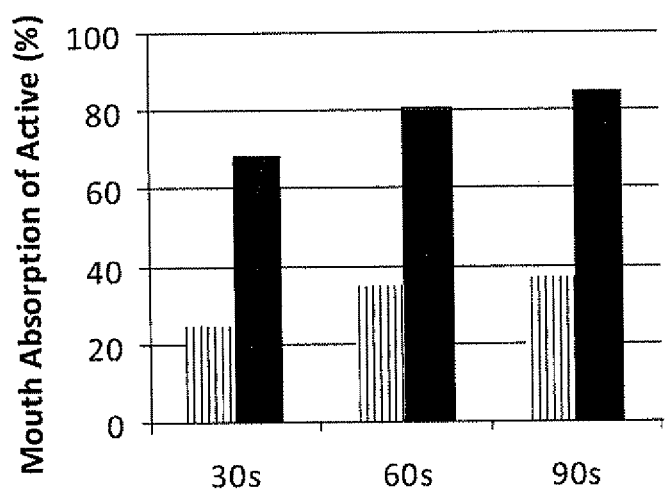
FIG. 6: Mouth absorption of active. Photospectroscopic detection of active(s) from *Hibiscus subdariffa* at 518 nm. Percentage of active mouth absorption calculated in function of the control (no mouth passage). The mouth absorption is compare the mastication process (black) and without mastication (vertical lines) with three mouth incubation/mastication time (30, 60 and 90 seconds).

As seen in FIG. 6, mastication allows absorption of active(s) by oral mucosa up to 86% after only 90 seconds.

EXAMPLE VII

Composition of Functional Chewing Gum
- a. Gum base amalgam: gum base:isomalt (approximately 1:3) 70-85%;
- b. Candelilla wax 0.5-5%
- c. Lauric acid; <4%
- d. $CO_2$ trapped sugar ($CO_2$ not from an acid and a carbonate reaction); 3-20%;
- e. Active ingredients: 0.5%-26%

All % are based on w/w.

EXAMPLE VIII

Composition of Functional Chewing Gum
- a. Gum base amalgam: gum base:isomalt (approximately 1:3) 70-85%;
- b. Candelilla wax 0.5-5%
- c. Lauric acid; <4%
- d. $CO_2$ trapped sugar ($CO_2$ not from an acid and a carbonate reaction); 3-20%;
- e. *Menthol crystal; 1-5% or Could be *WS-3 0.5%;
- f. *Flavor (e.g. Peppermint); 2.5%;
- g. *Sweetener (e.g. Neotame); 0.0002-0.1%;
- h. Active ingredients: 0.5%-26%

Ingredients marked with * in this example can be absent, present or replaced. The % of the remaining ingredients would then be adjusted accordingly.

All % are based on w/w.

EXAMPLE IX

Composition of Functional Chewing Gum
- a. Gum base amalgam: gum base:isomalt (approximately 1:3); 80%
- b. Candelilla wax; 0.5%
- c. Lauric acid; 3.0%
- d. $CO_2$ trapped sugar ($CO_2$ not from an acid and a carbonate reaction); 7.5%
- e. *Menthol crystal; 2.5%;
- f. *Peppermint flavor; 2.5%;
- g. *Neotame as a sweetener; 0.0002%;
- h. Active ingredients: 0.4%

Ingredients marked with * in this example can be absent, present or replaced. The % of the remaining ingredients would then be adjusted accordingly.

All % are based on w/w.

EXAMPLE X

Functional Chewing Gum
- a) Gum base amalgam: gum base: isomalt (approximately 1:3); 80% (70-85%);
- b) Candelilla wax; 1.0% (0.5-5%)
- c) Phospholipids >60% (Phosphatidylcholine, Phosphatidylethanolamine, Phosphatidylinositol, Phosphatidic acid). 4% (<8%);
- d) $CO_2$ trapped sugar ($CO_2$ not from an acid and a carbonate reaction); 5% (<20%);
- e) Menthol crystal/peppermint; 3.5%;
- f) Sucralose 1.0%
- g) Active ingredients: 5.5% of Angelica sinensis root extract

MCF: 4

All % are based on w/w.

Functional Chewing Gum 2
- a) Gum base amalgam: gum base: isomalt (approximately 1:3); 80% (70-85%);
- b) Candelilla wax; 1.0% (0.5-5%)
- c) Lauric acid; 3.0% (<4%)
- d) $CO_2$ trapped sugar ($CO_2$ not from an acid and a carbonate reaction); 5% (3-20%);
- e) Menthol crystal/peppermint; 2.5% (1-5%);
- f) Stevia 0.5%
- g) Active ingredients: 8% of Colostrum

MCF: 4

All % are based on w/w.

EXAMPLE XI

Natural Chewing Gum
- a. Manilkara zapotilla (Chicle) 50% (30-70%);
- b. Candelilla wax; 1.0% (0.1-5%);
- c. Lauric acid; 3.0% (<4%);
- d. $CO_2$ trapped sugar ($CO_2$ not from an acid and a carbonate reaction); 5% (1-20%);
- e. Menthol crystal; 2.0% (1-5%);
- f. Peppermint flavor; 2.0%;
- g. Sucralose 2.0%;
- h. Mannitol 25%;
- i. Active ingredient: Angelica sinensis root extract (10%).

MCF: 3

All % are based on w/w.

All ingredients are mix and compress to form a chewable amalgam.

EXAMPLE XII

Figure 8:
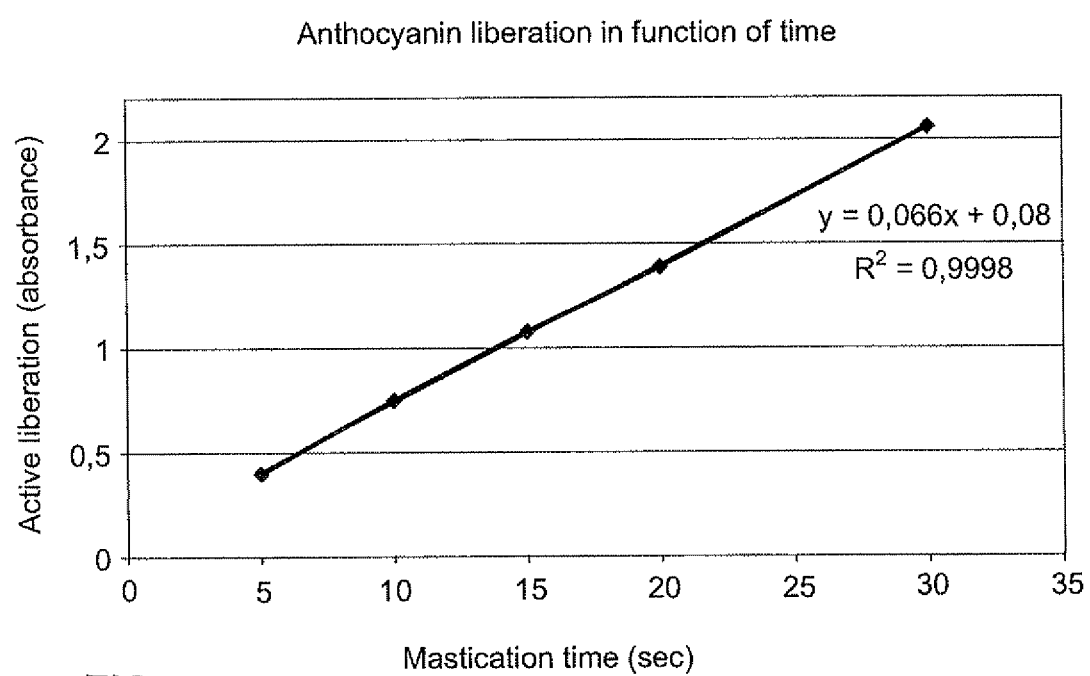
FIG. 8: Liberation of active(s) at 518 nm from *Hibiscus subdariffa* chew, in function of time.

Active Chew Liberation in Function of Mastication Time
- Preparation of Natural chewing gum (see Example XI) with Chicle of 1.35 mm particle size (granulometry). The active is any active as described herein (e.g. an extract of *Hibiscus Subdariffa*);
- Artificial mastication of one chew in 10 ml of water (or artificial saliva; to be defined); Artificial mastication: use a mortar/pestle corresponding to the buccal cavity, to mimic the compression force on a standardize manner (force, temperature, compression/minute . . . ).
- The absorbance of the extruded liquid extract is analysed by methods well known in the art (e.g for *Hibiscus Subdariffa* spectrophotometer at 518 nm);
- Time of mastication vary from 5 seconds to 30 seconds.
- FIG. 8 shows that it is possible to vary the release of actives from the dosage form. FIG. 8 also shows that there is a linear relation between the liberation of active during the fast release.

EXAMPLE XIII

Liberation of Actives in Function of the Granulometry of the Chews
- Preparation of Natural chewing gum (see Example XI) with Chicle of different particle size (granulometry). The active is any active as described herein (e.g. an extract of *Hibiscus Subdariffa*); The size of the particles vary from 0.7 mm to 2 mm;

Artificial mastication of one chew in 10 ml of water (or artificial saliva; to be defined). There are 3 mastication time: 10, 20 and 30 seconds;

The absorbance of the extruded liquid extract is analysed by methods well known in the art (e.g for *Hibiscus Subdariffa* spectrophotometer at 518 nm).

FIG. 9 shows that it is possible to vary the release of actives from the dosage form with the particle size.

EXAMPLE XIV

Sugar-$CO_2$

Variation of pH in Function of the Granulometry of the Sugar-$CO_2$

Figure 7A:
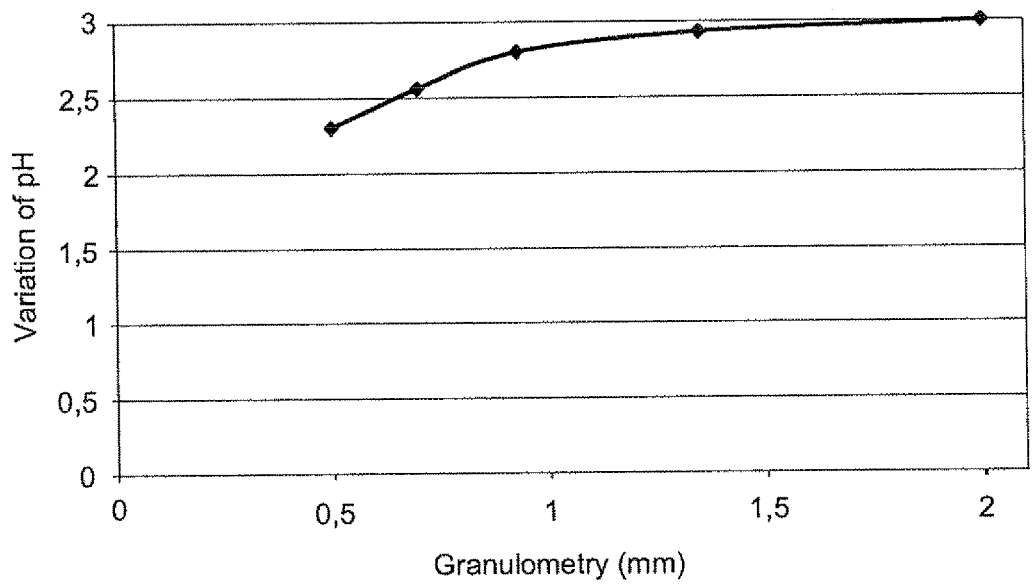
FIG. 7A: Variation of pH in function of the granulometry of the Sugar-$CO_2$. The concentration of the Sugar-$CO_2$ is 10% (w/v). The pH variation is calculated by the subtraction of the pH at the beginning and the pH after complete solubilisation of the Sugar-$CO_2$.

Prepare sugar-$CO_2$ with different particle size: 0.5 mm to 2 mm;

Add 10% (w/v) of Sugar-$CO_2$ in 20 ml of agitated distilled water, and note the decreased of pH with a pH meter;

Maximum pH decrease is 3 (at high particle size: 2 mm). Even at very low particle size (0.7 mm), the decrease of pH is still very high (2.3). See FIG. 7a.

EXAMPLE XV

Variation of pH in Function of the Concentration of Sugar $CO_2$

Figure 7B:
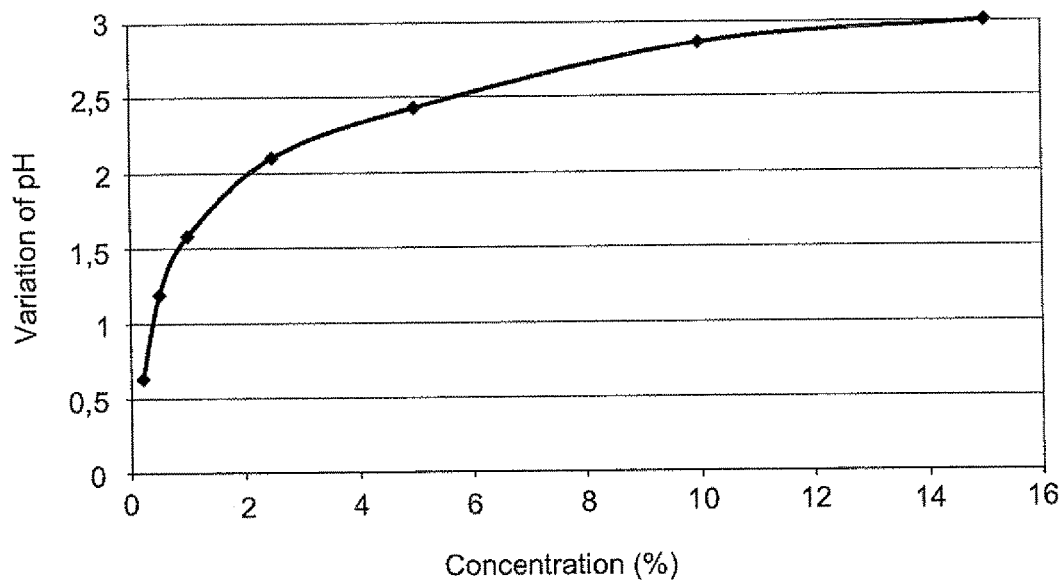
FIG. 7B: Variation of the pH in function of the concentration of the Sugar-$CO_2$. Granulometry of the Sugar-$CO_2$ is 1.35 mm.

Add different concentration (02% to 15% w/v) of Sugar-$CO_2$ (particle size of 1.35 mm) in 20 ml of agitated distilled water, note the decreased of pH with a pH meter;

The variation of pH follow a logarithmic function (y=0.55 ln(x)+1.56); See FIG. 7b.

EXAMPLE XVI

Effect of Saliva on the Delivery of the Active by the Chewable Vehicle

Chewing gums are prepared following example xx, containing a bark extract of Corynanthe yohimbe (containing 8% of yohimbine);

Gums are artificially masticated for 120 seconds in 10 ml of water or artificial saliva;

The quantity of released yohimbine is analysed by chromatography.

Figure 10:
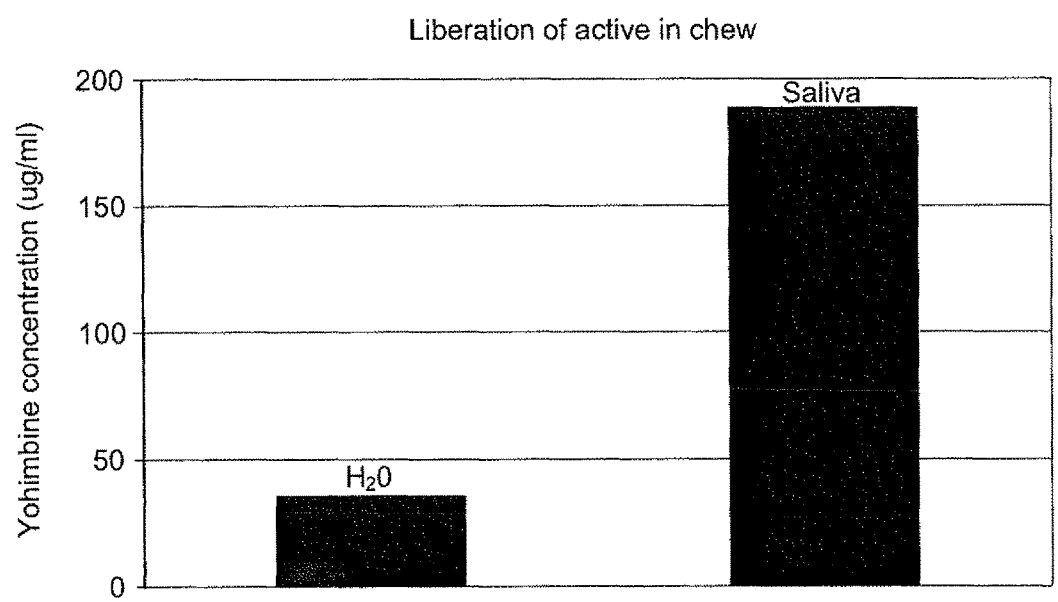
FIG. 10: Comparison of the water and saliva liberation of active (yohimbine) in chew. The chew was masticated 2 minutes.

The quantity of yohimbine released is more than 5 time when is masticated in saliva than in water. The effect of bolus (enzymes, texture . . . ) on the release of active is shown on FIG. 10.

EXAMPLE XVII

Absorption of Active(s) by Mouth Mucosa and Penetration in the Blood

The absorption of active ingredients in the blood of a human volunteer with a chewable vehicle of the invention can be determined by methods well know in the art (Remington: The Science & Practice of Pharmacy 21th Edition, Lippincott Williams and Wilkins, Philadelphia, Pa. (2005)). For example, the active ingredient can be formulated in a chewable formulation (the "Active Chew") according to the invention and given to healthy volunteers. In order to determine the effect of mastication, one can compare the blood levels of the active ingredient or a metabolite thereof following consumption of the chewable formulation when the Active Chew is masticated or simply swallowed.

In an other embodiment, instead of the measuring the blood level of the active ingredient, the biological effect can be monitored following administration of the Active Chew.

In one embodiment, the following protocol can be followed to study the effect of the chewable vehicle on the absorption of the active ingredient.

1) Cohort
   6 volunteers age from 20 to 55 years old.
2) Chewable Material
   Each chew ha san average of 2.0 g and comprises about 150 mg of active extract mix or ingredients.
3) Administration
Swallow the Gums
   1 or 2 gums are cut in small pieces and swallow with water without chewing (control).
Chewing the Gums
   The gums were chewed 10 minutes after the glucose load.
4) Blood Absorption
   Measure of the blood levels or biological effect of active extract mix or ingredients according to methods well known in the art.

EXAMPLE XVIII

Buccal Mucosa Absorption of Active Ingredient

Chewing gums are prepared following example VIII, containing an an active ingredient as described herein. Gums are artificially masticated for 120 seconds in 10 ml of artificial saliva. The quantity of released active ingredient is used in the EpiOral™ 3D-human buccal mucosa tissue.

EpiOral™ purchased from MatTek Corp. (Ashland, Mass.) is used for those experiments. This model, a 3D-human buccal mucosa tissue, is an 8-11 cell layered tissue consisting of an organized basal layer and multiple non-cornified layers, with the characteristics of native buccal tissue differentiated from human primary oral keratinocytes.

On the day of treatments, 0.3 mL of EpiOral media warmed to 37° C. is dispensed into every well of a 24-weel plate. The EpiOral™ constructs cultured on the surface of tissue inserts are transferred aseptically into the media filled 24 well plates. The tissues are then incubated at 37° C. in a humidified atmosphere of 5% $CO_2$ for at least 1 hour. The inserts are then transferred into a new 24-well plate containing 0.3 of Hank's buffered solution (HBSS).

The EpiOral™ tissue culture inserts are treated with test materials or artificial saliva and returned to the incubator. At specific time intervals, the tissues are moved into a new 24-well plate. The receiver solution at each time point is kept for further analysis of the active ingredient content.

After 90 minutes of total permeation time, the tissue integrity is checked.

Measurement of Active Ingredient Concentration

Active ingredient concentrations are measured by ultra-performance liquid chromatography coupled to tandem mass spectrometry (UPLC-MS/MS). The receiver solutions are quantified without any dilutions. The mass spectrometer is operated in MRM mode and an electrospray ionisation source is used. The compound is retained 5 minutes in the chromatographic system and the transition 449>287 m/z is monitored in positive mode.

Flux Calculation: The amount (nmole) of active ingredient in each sample is converted to nmole/$cm^2$ assuming that the area of one EpiOral™ tissue is 0.6 $cm^2$. Cumulative nmole/$cm^2$ values are plotted as cumulative penetration (nmole/$cm^2$) versus time where the slope of the linear regression is used to calculate the steady state flux ($J_{ss}$).

In one aspect, the Khlôros vehicle contribute to accelerate the steady state flux (absorption) compared to the active only in saliva.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A chewable composition for buccal mucosal absorption of a pharmacologically active ingredient in a subject wherein said chewable composition comprises:
   a particulate amalgam matrix comprising:
      a gum base in particulate form
      the active ingredient in powder form; and
      sugar particles containing entrapped-$CO_2$, the sugar particles having a diameter between about 0.5 mm and about 1 mm;
   in admixture with a modulatory mixture comprising lecithin; and a texture modulator selected from the group consisting of Candelilia wax and Carnauba wax support, wherein lecithin or lauric acid and said texture modulator waxes are in a ratio suitable to achieve a melting point of about 36° C.
wherein said chewable composition, is suitable for increasing the absorption of the active ingredient in the buccal mucosa by at least about 2 x after being chewed for 30 to 120 seconds as compared to a particulate composition devoid of the sugar particles and modulatory mixture.

2. The chewable composition of claim 1, wherein said composition is in particulate form and is compressed to form a chewable dosage form having a Matrix Cohesive Force (MCF) between 2 and 5.

3. The chewable composition of claim 1, wherein said composition comprises 20% to 60% (w/w) of said amalgam matrix.

4. The chewable composition of claim 1, wherein said composition comprises from 0.5 to 15% (w/w) of the lecithin and from 0.1 to 6% (w/w) of the texture modulator.

5. The chewable composition of claim 1, wherein the composition comprises about 20% w/w to about 90% w/w of the particulate gum base.

6. The chewable composition of claim 1, Wherein the particulate amalgarn matrix comprises particles having a size greater than about 0.9 mm.

7. The chewable composition of claim 6, wherein the composition comprises about 5% w/w of the $CO_2$-sugar particles.

8. The chewable composition of claim 1, wherein the active ingredient is selected from the group consisting of: Guarana, Black cohash (Cimicifuga racemose), *Ginseng* (*Panax*spp.), Hops (*Humulus Lupulus*),*Rhodiola Rosea*, Tumeric (*Curcuma longa*), Astaxanthin, Coenzyme $Q_{10}$, Curcumine, Glucosamine, Melatonin, Resveratrol, gingerol, and combinations thereof.

9. The chewable composition of claim 1, wherein the active ingredient is selected from the group consisting of: phytosterol, which is chosen from diosgenine, brassicasterol, carmpsterol, 5α-cholestane, β-sitosterone, β-sitosterol, stigmasterol, and combinations thereof.

10. The chewable delivery dosage form of claim 1, wherein the gum base comprises polyols.

11. The chewable delivery dosage form of claim 1, wherein the active ingredient is selected from the group consisting of:
   NSAIDs; Beta-receptor blockers; Vasodilators; Antiarrhytmics; Antibiotics; Ion channel blockers; Antispasmodics; Anaesthetics; Diphosphonates; Diuretics; Stimulants; Antihistamines; Angiotensin-Converting Enzyme (ACE) Inhibitors; Antiviral drugs; Antiemetics; Vasoconstrictors; Dopamine agonists/antagonists; Proton pump inhibitors; Antidiabetics;H2 receptors antagonists; Antidepressants; 5-HT antagonists; Anxiolytics; Hypnotics; Muscle relaxants; Anticholinergics; Somatostatine inhibitors; Antioxidants; Angiotensin receptor blockers; Steroids and Steroids hormone receptor; Oestrogens; Statins; and combination thereof.

12. The chewable Composition of claim 1, wherein the active ingredient is a stimulant.

13. The chewable delivery dosage form of claim 1, wherein the active ingredient is selected from the group consisting of:
   a) ion channel biockers, reflux suppressants, antiflatulents, antidopaminergics, proton pump inhibitors, H2-receptor antagonists, cytoprotectants, prostaglandin and prostaglandin analogues, laxatives, antispasmodics, antidiarrheals, bile acid sequestrants, opioids, beta-receptor blocker, diuretics, cardiac *glycosides*, antiarrhytmics, nitrate, antiamgials, vasoconstrictor, vasodilators, peripheral activators, ACE inhibitors, angiotensin receptor blockers, alpha-blocker, anticoagulants, heparin, antiplatelet drugs fibrinolytics, antihemophilic factors, haemostatic drugs, hypolipidaemic agents, statins, hyphotics, anaesthetics, antipsychotics, antidepressants, antiemetics, anticonvulsants/antiepileptics, anxiolytics, barbiturates, folic acid, phenolic compounds, movement disorder drugs, stimulants, benzodiazepine, cyclopyrrolones, dopamine agonists/antagonists, antihistamines, bromide, scopolamine, cholinergics, anticholittagics, emetics, cannabinoids, 5-HT antagonists, NSAIDs, oploids, paracetamol, muscle relaxant, neuromuscular drugs, anticholinesterases, adrenergic blockers, antibotics, aminoglycosides, sulfa drugs, fluoroquinolones, antiviral drugs, anti-fungal, corticosteroids, mast cell inhibitors, prostaglandin agonists/inhibitors, steroids, antiseptcs, anesthetics, androgens, antiandrogens, gonadotropin, human growth factor, insulin, antidiabetics, thyroid hormones, antityroid drugs, calcitonin, diphosponate, vasopressin analogues, quinolones, 5-alpha reductase inhibitor, selective alpha-1 blockers, sildenafils, tadalafils, fertility drugs, hormonal contraception, ormeloxifene, antifibrinolytics, follicle stimulating, hormone, luteinising hormone, gamolenic acid, gonadotropin release inhibitor, progestin, oestrogen, gonadorelin, clomiphene, tamoxifen, diethyl stibestrol, antileprotics, antituberculous drugs, antimalarials, anthelmintics, amoebicides, antivirals, antiprotozoals, vaccines, immunoglobulins, immunosuppresants, interferons, monoclonal antibodies, antiallergics, cytotoxic drugs, therapeutic antbodies, somatostatin inhibitors, recombinant interleukins, G-CSF, erythropoietin, vitamins, antioxidants and combinations thereof;
   b) Astaxanthin, Bilobalide, Biotine, Catechine, Choline, Coenzyme Q10, Curcumine, Ginkgolide, Glucosamine, Hypericine, Hynerforin, Silymarine, Silibinin, a Lignan, Diosgenine, hydroxycitric acid, eleutherocide B, Eleutherocide E,L-carnitine Megastigmane glycoside, Melatonin, Niacinamide, Niacine, Ornega-3, Pantothenic acid, a phytosterol, Pinolenic acid, Resveratrol, Riboflavine, Rosiglitazone, Serotonin, Theobromine, Theophylline, Thiamine, g-aminobutyric acid, a saponin, sarsapic acid, Vitamin B12, Yohimbine, gingerol, or combinations thereof;

or c) a plant extract selected from the group consisting of Absinthe (*Artemisia absinthum*),Alfalfa (*Medicago sativa*), Aloe (*Aloe barbadensis*), Angelica (*Angelica archangelica*and *sinensis*), Arnica (*Arnica montana*), Ashwaganda (*Withania somnifera*), Astragalus (*Astragalus membranaceus*), Betony (*Stachys/Betonica officinalis*), Bilberry/Huckleberry (*Vaccinium*spp.), Black cohash (*Cimicifuga racemose*), Bladderwrack (*Fucus versiculosus*), Blessed thistle (*Cnicus benedictus*), Blue cohosh (*caulophyllum thalictroides*), Boneset (*Eupatorium perforaturn*), Burdock (*Arctium lappa*), *Caesalpinia benthamiana*, Calendula ((*Calendula officinalis*), California poppy (*Eschscholzia Californica*), Caraway (*Carum carvi*), Cardamom (*Elettaria cardamomum*), Cascara (*Rhamnus purshiana*), Catnip (*Nepeta cataria*), Cayenne (*Capsicum frutescens*), Cedar, Western (*Thuja plicata or occidentalis*), Chamomile (*Matricaria recutita*), Chaparral (*Larrea Mexicana*), Chaste tree berry (*Vitex agnus castus*), Chickweed (*Stenaria media*), Cleavers (*Galium aparine*), Coltsfoot (*Tussliago farfara*), Comfrey (*Symphytum officinalis*), Corn silk (*Zea mays*), *Corynanthe yohimbe*,Cramp bark (*Viburnum opulus*), Dandelion (*Taraxacum officinalis*), Devils club (*Oplopariax horridus*), Dioscorea villosa, Dong quai (*Angeica sinensis*), Echinacea(*Echinacea*spp.), Elder flowers (*Sambucus*spp.), Elecampane (*Inula helenium*),Eyebright (*Euphrasia officinalis*), Fadogia agrestis, Fennel (*Foeniculum vulgare*), Fenugreek (*Trigonella foenum-graecum*), Feverfew (*Tanaceturn parthenium*), Flax seed (*Linum usitatissimum*),Garcina Cambogia, Garlic (*Allium sativa*), Geranium(*Geranium maculatum*), Ginger (*Zingiber officinalis*), Ginkgo (*Ginkgo biloba*), *Ginseng* (*Panax*spp.), Goldenrod (*Solidago*spp.), Goldenseal (*Hydrastis canadensis*), Gotu kola (*Centella asiatica*), Gravel root (*Eupatorium purpureum*), Hawthorne (*Crataegus*spp.), *Hibiscus subdariffa*, Hops (*Humulus lupulus*), Horehound (*Marrubium vulgaris*), Horsetail (*Equisetum arvense*), *Hippophae rhamnoides,*Hyssop (*Hyssopus officinais*), Kava kava (*Piper methysticum*), Lady's mantle (*Alcehemilla vulgaris*), *Lepidium meyenii*, Linden flower (*Tilia*spp.), Lobelia (*Lobelia inflata*), Lomatium (*Lomatium dissectum*), Lungwort (*Sticta pulmonaria*), Marshmallow (*Althea officinalis*), *Massularia acuminate*, Meadowsweet (*Filipendula ulmaria*), Microdesmis keayana, Milk thistle (*Silybum marianum*), Morinda citrifolia, Motherwort (*Leonurus cardiaca*), Mucuna pruriens, Mugwort (*Artemisia vulgaris*), Mullein (*Verbascum thapsus*), Myrrh gum (*Commiphora indica*), Nettle (*Urtica*spp .), Noni (*Morinda citrifolia*), Nopal (*Opuntia ficus indica*), Oat (*Avena sativa*), *Oenothera biennis*, Old man's beard, Usnea (*Usnea*spp.), Oregon grape root and barberry (*Mahonia*spp.), Osha (*Ligusticum porteri*), Parsley (*Petroselinum crispum*), Plantain (*Plantago*spp.), Poplar buds (*Populus*spp.), Red clover (*Trifolium pratense*), Red root (*Ceanothus americanus*), *Rhodiola Rosea*, Rosemary (*Rosmarinus officinalis*), Sage (*Salvia officinalis*), Saint John's wort (*Hypericum perforatum*), Saw palmetto (*Serenoa repens*), Sea-buckthorn (*Hippophae rharmnoides*), Sesame seed (*Sesamum indicum*), Siberian ginseng (*Eleutherococcus senticosus*), Skullcap (*Scutellaria laterifolia*), Slippery elm (*Ulmus*spp. (*rubra, fulva*)), Thyme (*Thymus vulgaris*), *Triblus terrestris*, Tumeric (*Curcuma longa*), *Thuya occidentalis*, Uva ursi (*Arctostaphylos uva ursi*), Valerian (*Valeriana officinalis*), Vervain (*Verbena officinalis*), White oak bark(*Quercus alba*), Willow (*Salix*spp.), Yarrow (*Achillea millefolium*), Yellow dock (*Rumex crispus/obtusifolius*), Guarana and combinations thereof.

14. The chewable composition of claim 1, wherein said particulate amalgam matrix is in the form of microspheres, spheres, or spheroids.

\* \* \* \* \*